(12) United States Patent
Famodu et al.

(10) Patent No.: US 6,969,785 B2
(45) Date of Patent: Nov. 29, 2005

(54) STEROL METABOLISM ENZYMES

(76) Inventors: Omolayo O. Famodu, 216 Barrett Run Pl., Newark, DE (US) 19702; Emil M. Orozco, Jr., 2 Dutton Farm La., West Grove, PA (US) 19390

(*) Notice: Subject to any disclaimer, the term of this patent is extended or adjusted under 35 U.S.C. 154(b) by 53 days.

(21) Appl. No.: 10/224,880

(22) Filed: Aug. 21, 2002

(65) Prior Publication Data

US 2003/0229914 A1 Dec. 11, 2003

Related U.S. Application Data

(62) Division of application No. 09/443,041, filed on Nov. 19, 1999, now Pat. No. 6,465,717.
(60) Provisional application No. 60/109,283, filed on Nov. 20, 1998.

(51) Int. Cl.[7] .................. A01H 1/00; C07H 21/04; C07K 14/415; C12N 5/14; C12N 9/00
(52) U.S. Cl. .................. 800/295; 435/6; 435/69.1; 435/468; 435/419; 435/252.3; 435/320.1; 435/183; 530/370; 536/23.6; 800/278
(58) Field of Search .................. 435/6, 69.1, 468; 435/419, 252.3, 320.1; 530/370; 536/23.6; 800/278, 295

(56) References Cited

PUBLICATIONS

Xu, G. et al., Blocking late cholesterol biosynthesis inhibits the growth of transplanted Morris hepatomas (7288CTC) in rats, Hepatology, Aug. 1996;24(2):440–445.
Moebuis, F.F. et al., Molecular cloning and expression of the human delta7–sterol reductase, Proc. Natl. Acad. Sci. U. S. A., Feb. 17, 1998;95(4):1899–18902.
Taton, M. and Rahier, A,. Identification of delta 5,7–sterol–delta 7–reductase in higher plant microsomes, Biochem. Biophys. Res. Commun., Nov. 27, 1991;181(1):465–473.
Lecain, E. et al., Cloning by metabolic interference in yeast and enzymatic characterization of *Arabidopsis thallana* sterol delta 7–reductase, J. Biol. Chem., May 3, 1996;271(18):10866–10873.
Arthington–Skaggs, B.A. et al., Positive and negative regulation of a sterol biosynthetic gene (ERG3) in the post–squalene portion of the yeast ergosterol pathway, FEBS Lett., Aug. 26, 1996;392(2):161–165.

Smith, S.J. and Parks, L.W., The ERG3 gene in *Saccharomyces cerevisiae* is required for the utilization of respiratory substrates and in heme–deficient cells, Yeast, Nov. 1993;9(11):1177–1187.
Smith, S.J. et al., Transcriptional regulation by ergosterol in the yeast *Saccharomyces cerevisiae*, Mol. Cell. Biol., Oct. 1996;16(10):5427–5432.
Matsushima, M. et al., Molecular cloning and mapping of a human cDNA (SC5DL) encoding a protein homologous to fungal sterol–C5–desaturase, Cytogenet. Cell Genet., 1996;74(4):252–254.
Pompon, D., et al., Sterol delta–7 reductase (*Arabidopsis thaliana*), NCBI General Identifier No. 1245182, Accession AAC49278, published May 9, 1996.
Beneviste, P., sterol–C5(6)–desaturase homolog [*Nicotiana tabacum*], NCBI General Identifier No. 4426627, Accession AAD20458, published May 19, 1999.
Husselstein, T., et al., Delta7–sterol–C5–desaturase: molecular characterization and functional expression of wild–type and mutant alleles, Plant Mol. Biol., 1999; 39 (5):891–906.
Beneviste, P., sterol–C5(6)–desaturase [*Nicotiana tabacum*]; NCBI General Identifer No. 4140398, Accession AAD04034, published May 19, 1999.
Taton, M. and Rahier, A. Plant sterol biosynthesis: Identification and characterization of higher plant delta 7–sterol C5(6)–desaturase, Arch. Biochem. Biophys., Jan. 15, 1996;325(2):279–288.
Geber, A. and Swartz, J.E., C–5 Sterol Desaturase, [*Candida glabrata*], NCBI General Identifier No. 1706691, Accession P50860, Published Oct. 1, 1996.
Gachotte, D. et al., Isolation and characterization of an *Arabidopsis thaliana* cDNA encoding a delta 7–sterol–C–5–desaturase by functional complementation of a defective yeast mutant, Plant J. Mar. 1996;9(3):391–398.
Geber, A., et al., Deletion of the *Candida glabrata* ERG3 and ERG11 genes: effect on cell viability, cell growth, sterol composition, and antifungal susceptibility, Antimicrob. Agents Chemother., Dec. 1995;39(12):2708–2717.

*Primary Examiner*—Phuong T. Bui
(74) *Attorney, Agent, or Firm*—Morgan & Finnegan, L.L.P.

(57) ABSTRACT

This invention relates to an isolated nucleic acid fragment encoding a sterol metabolism enzyme. The invention also relates to the construction of a chimeric gene encoding all or a portion of the sterol metabolism enzyme, in sense or antisense orientation, wherein expression of the chimeric gene results in production of altered levels of the sterol metabolism enzyme in a transformed host cell.

11 Claims, 4 Drawing Sheets

```
[                                                                                                                60]
SEQ_ID_NO_2              ------------------------TVHSALVTYTSMLALLSLCPPFVILLWYTMVHADGSVVRT
SEQ_ID_NO_18             K-----------------------TVHSALVTYTSMLSLLSLCPPFVILLWYTMVHADGSVVRA
SEQ_ID_NO_20             MGA---------------------TVHSPLVTYASVISLLTLCPPFVILLWYTMTLADGSVSET
SEQ_ID_NO_22             MAKPKPSSAGAKPTAAAPPVTVHSALVTYTSMLALLSLCPPFVILLWYTMVHADGSVVRT
Arabidopsis_gi|245182    MAE---------------------TVHSPIVTYASMLSLLAFCPPFVILLWYTMVHQDGSVTQT

[                                                                                                               120]
SEQ_ID_NO_2              YEHLRDHGV-DGLKAIWPMPTLVAWKISAAVGLSE------------------------------
SEQ_ID_NO_18             YEHLREHG-LEGLKAIWPMPTMAAWKIIFGFGLFEAALQLLLPGKRFEGPVSPSGNVPVY
SEQ_ID_NO_20             FHYLRQNG-LQGLLHIWPTPTPTACKIIAVYAAFEAALQLLLPGKTVYGPISPTGHRPVY
SEQ_ID_NO_22             YEHLRDHGVLEGLKAIWPMPTLVAWKIIFGFGLFEAVLQLLLPGKRFEGPISPAGNVPVY
Arabidopsis_gi|245182    FGFFWENG-VQGLINIWPRPTLIAWKIIFCYGAFEAILQLLLPGKRVEGPISPAGNRPVY

[                                                                                                               180]
SEQ_ID_NO_2              KANGLQAYAVTLITYLSLWWFGIFNPAIVYDHLGEIYSALVFGSFVFCIFLYIKGHLAPS
SEQ_ID_NO_18             KANGLQAYFVTLITYFALWWFGIFNPTIVYHHLGEIYSALIFGSF_FCVFLYIKGHLAPS
SEQ_ID_NO_20             KANGLQAYAVTLITYLGLWWFGIFNPAIVYDHLGEIYSALVFGSFVFCIFLYIKGHVFPS
SEQ_ID_NO_22             KANGLAAYFVTLATHLGLWWFGIFNPAIVYDHLGEIFSALIFGSFIFCVLLYIKGHVAPS
Arabidopsis_gi|245182

[                                                                                                               240]
SEQ_ID_NO_2              SSDSGSSGNVIIDFYWGMELYPRIGKHFDIKVFTNCRFGMMSWAVLAVTYCIKQYEMNGR
SEQ_ID_NO_18             STDSGSSGNLIIDFYWGMELYPRIGKHFDIKVFTNCRFGMMSWAVLALTYCIKQYEENGK
SEQ_ID_NO_20             SSDSGSSGNVIIDFYWGMELYPRIGKHFDIKVFTNCRFGMMSWAVLAVTYCIKQYEMNGR
SEQ_ID_NO_22             
Arabidopsis_gi|245182    SSDSGSCGNLIIDFYWGMELYPRIGKSFDIKVFTNCRFGMMSWAVLAVTYCIKQYEINGK
```

FIG. 1A

```
[                                                                              300]
SEQ_ID_NO_2              ----------------------------------------------------------
SEQ_ID_NO_18         241 VADSMLVNTALMLIYVTKFFWESGYWCTMDIAHDRAGFYICWGCLVWPSIYTSPGMYL
SEQ_ID_NO_20             VADSMLVNTALMLVYTKFFWEAGYWSTMDIAHDRAGFYICWGCLVWVPSVYTSPGMYL
SEQ_ID_NO_22             VADSMLVNTALMLIYITKFFWESGYWCTMDIAHDRAGFYICWGCLVWVPSIYTSPGMYL
Arabidopsis_gi|245182    VSDSMLVNTILMLVYTKFFWEAGYWNTMDIAHDRAGFYICWGCLVWVPSVYTSPGMYL

[                                                                              360]
SEQ_ID_NO_2              ----------------------------------------------------------
SEQ_ID_NO_18         301 VNHPVNLGPQLALSISLLAGILCIYINYDCDRQRQEFRRTNGKCSIWGKAPSKIVASYQTT
SEQ_ID_NO_20             VNHPVNLGIKLALSILVAGILCIYINYDCDRQRQEFRRTNGKGTVWGKAPSKIEATYTTT
SEQ_ID_NO_22             VNHPLNLGPQLALSILLAGMLCIYINYDCDRQRQEFRRTNGKCSVWGKAPSKIVASYQTT
Arabidopsis_gi|245182    VNHPVELGTQLAIYILVAGILCIYIKYDCDRQRQEFRRTNGKCLVWGRAPSKIVASYTTT

[                                                                              420]
SEQ_ID_NO_2              ----------------------------------------------------------
SEQ_ID_NO_18         361 NGETKSSLLLTSGWWGLSRHFHYVPEILSAFFWTVPALEDHFLPYFYVIFLTILLFDRAK
SEQ_ID_NO_20             SGETKRSLLLTSGWWGLSRHFHYVPEILAAFFWTVPALFEHEFLPYFYVIFLTILLFDRAK
SEQ_ID_NO_22             KGETKTSLLLTSGWWGLSRHFHYVPEILSAFFWTVPALFNHFLPYFYVIFLTILLFDRAK
Arabidopsis_gi|245182    SGETKTSLLLTSGWWGLARHFHYVPALFDNFLAYFYV--LTLLLFDRAK

[                                                      450]
SEQ_ID_NO_2              -----------------------------------------
SEQ_ID_NO_18         421 RDDDRCSSKYGKYWKMYCNKVPCRVIPGIY
SEQ_ID_NO_20             RDDDRCRSKYGKYWKLYCDKVPYRIIPGIY
SEQ_ID_NO_22             RDDDRCSSKYGKYWKLYCNKVPYRVIPGIY
Arabidopsis_gi|245182    RDDDRCRSKYGKYWKLYCEKVKYRIIPGIY
```

FIG. 1B

```
                                                                              60]
tobacco_gi4426627   1 MDDYLNLFIEETSFYNRVVLGTFLPESWWGPLPHWFQGWLRNYIGGVLLYFISGFLWCFY
SEQ_ID_NO_24          --EYLRQFVEETAWYNEIFLSHVVPGDWWRALPHPLQSWLRNGLGGYLIYFACGFLWCFV
SEQ_ID_NO_26          --EYSRLFGEDTDLYNRIVLGALLPHSVWGPLPRFLQTWLRNYLGVLLYLLSGLLWCFY
SEQ_ID_NO_28          ------------------------------WWRALPHPLRSWLRNCIGGYLLYFATGFLWCFV
SEQ_ID_NO_30          ------------------------------WWRALPHPLRSWLRNCIGGYLLYFATGFLWCFV
tobacco_gi4140398     MEDYLKQFVEETSFYNRLVLG=EMPESWWGPLPHMLQGWLRNYIGGVLLYFISGFLWCFY 120]
tobacco_gi4426627  61 IYRLKRNVYIPKDAIPSNRAMLLQIGVAMKAMPFYCALPSLSEYMIVNGWTKCFSRISDV
SEQ_ID_NO_24          ------DAIPTNEAMKKQIAVASKAMPFYCALPTLSEYMIESGWTRCYFNISEM
SEQ_ID_NO_26          IYYWKRHAYIPKDSIPTIEAMKKQIIVASKAMPLYCALPTLSEYMVENGWTQCYVNISEV
SEQ_ID_NO_28          IYYWKRNVHVPKDAIPSQRAMLEQISVAMKAMPWYSLLPTVSEYLVETGWTKCYPRLYNV
SEQ_ID_NO_30          IYYWKRNAYIPKDAVPTVEAMKKQIIVASKAMPFYCALPSVSEHMIESGWTRCFFHISEV
tobacco_gi4140398     IYHLKRNVYIPKDAIPSNKAMLLQISVAMKAMPWYCALPSLSEYMIENGWTKCFARISDV 180]
tobacco_gi4426627 121 GWLSYLIYMAVYLVIVEFGIYWMHRELHDIKLLYKLHATHHIYNKQNTLSPFAGLAFHP
SEQ_ID_NO_24          GFSAYLCYMAMYLIFVEEFGIYWMHRELHDIKPLYKHLHATHHIYNKENTLSPFAGLAFHP
SEQ_ID_NO_26          GWPMYLVYLALYLIFVEFGIYWMHRELHDIKPLYKLHTYHHIYNKENTLSPFAGLAFHP
SEQ_ID_NO_28          GWLAYLVYLAIYLIIVEFVEFGIYWMHRELHDIKPLYKLHATHHIYNKQNTLSPFAGLAFHP
SEQ_ID_NO_30          GWPMYIIYVSLYLIFVEFGIYWMHRELHDIKPLYKHLHATHHIYNKENTLSPFAGLAFHP
tobacco_gi4140398     GWLSYVIYAAIYLVIVEFGIYWMHMELHDIKPLYKYLHATHHIYNKQNTLSPFAGLAFHP
```

FIG. 2A

```
[                                                                                                               240]
tobacco_gi4426627    181 LDGILQAVPHVVALFLLPEHFTTHIALLFIEAIWTANIHDCKHAKVWPVMGAGYHTIHHT
SEQ_ID_NO_24             LDGILQAIPHVLALFLLPTHFERTHIALVLFLEGVWTTNIHDCIHGKVWPVMGAGYHTIHHT
SEQ_ID_NO_26             LDGILQAIPHVFALYLIPTHFRTHIALLFIEAVWTTNIHDCIHGKVWPVMGAGYHTIHHT
SEQ_ID_NO_28             LDGILQALPHSLCLFFMPIHFTTHLALIFIEGVWTANIHDCIHGKLWPVMGAGYHTIHHT
SEQ_ID_NO_30             LDGILQAISHVIALFLLPMHFRTHIALLFIEAVWTANIHDCIHGKIWPVMGAGYHTIHHT
tobacco_gi4140398        LDGILQAVPHVVALLLVPMHFSTHIALIFLEALWTANIHDCIHGKVFPVMGAGYHTIHHR

[                                      271]
tobacco_gi4426627    241 TYRHNYGHYTIWMDWMFGTLRDPVEDEVKKM
SEQ_ID_NO_24             TYRHNYGHYTVWMDWMFGTLREP---------
SEQ_ID_NO_26             TYRHNYGHYTVWMDWMFGTLREP---------
SEQ_ID_NO_28             TYRHNYGHYTVWMDWMFGTLRDPEEDGGKAM
SEQ_ID_NO_30             TYRHNYGHYTVWMDWLFGTLREP---------
tobacco_gi4140398        TYRHNYGHYTIWMDWMFGTLRDPVEEDAKKM
```

FIG. 2B

SEQUENCE LISTING

<160> NUMBER OF SEQ ID NOS: 33

<210> SEQ ID NO 1
<211> LENGTH: 624
<212> TYPE: DNA
<213> ORGANISM: Zea mays

<400> SEQUENCE: 1

```
cgggctgcag gattcggcac gaggctgctg ctcctctcct cccatctcac cacacaccgc      60
agccccagca agatcgcgcg gaggccatgg cgaaccaagc cttcctccgc cggcgccaag     120
ccgaccgcgg ctgcgccacc ggttacagtg cactcggcgc tggtcaccta cacctccatg     180
ctcgcgctcc tctccctctg cccgcccttc gtcatcctcc tgtggtacac gatggtgcac     240
gcggacggat cggtggtgcg gacttacgag cacctcaggg atcacggcgt gctcgatggg     300
ctcaaggcca tctggcccat gccacccctc gtcgcgtgga agatatctgc ggctgtaggg     360
ctctcggaga cggccgaagg atggtggcac ttgggagcct tcggagggcc aactctgttg     420
ccgggaagtc cggtctacaa cgatatgctt acaacatgtc agtgacttga tacttacttg     480
gttgtggtgt cggtaattag cctcaatagt gatgctactt ggggagaatc tctctcatgt     540
tttggagctt gtggtcgaga tttcctaata gagggcatgt attcgacgta gctgctctgg     600
tcgctgggat gtaaatgctt cagg                                            624
```

<210> SEQ ID NO 2
<211> LENGTH: 74
<212> TYPE: PRT
<213> ORGANISM: Zea mays

<400> SEQUENCE: 2

```
Thr Val His Ser Ala Leu Val Thr Tyr Thr Ser Met Leu Ala Leu Leu
  1               5                  10                  15

Ser Leu Cys Pro Pro Phe Val Ile Leu Leu Trp Tyr Thr Met Val His
             20                  25                  30

Ala Asp Gly Ser Val Val Arg Thr Tyr Glu His Leu Arg Asp His Gly
         35                  40                  45

Val Asp Gly Leu Lys Ala Ile Trp Pro Met Pro Thr Leu Val Ala Trp
     50                  55                  60
```

```
Lys Ile Ser Ala Ala Val Gly Leu Ser Glu
 65                  70
```

<210> SEQ ID NO 3
<211> LENGTH: 533
<212> TYPE: DNA
<213> ORGANISM: Oryza sativa
<220> FEATURE:
<221> NAME/KEY: unsure
<222> LOCATION: (391)
<223> OTHER INFORMATION: n = A, C, G, or T
<220> FEATURE:
<221> NAME/KEY: unsure
<222> LOCATION: (428)
<223> OTHER INFORMATION: n = A, C, G, or T
<220> FEATURE:
<221> NAME/KEY: unsure
<222> LOCATION: (459)
<223> OTHER INFORMATION: n = A, C, G, or T
<220> FEATURE:
<221> NAME/KEY: unsure
<222> LOCATION: (492)
<223> OTHER INFORMATION: n = A, C, G, or T
<220> FEATURE:
<221> NAME/KEY: unsure
<222> LOCATION: (505)
<223> OTHER INFORMATION: n = A, C, G, or T

<400> SEQUENCE: 3

```
cttacactca ctcgatctcc ttcctccact gtcgctcaga tcgacgcggg ccatgccaa      60
gcctagggcc tccgccgccg cggcgaaggc gccagcctcc acgccgccca agacggtgca    120
ctcggcgctc gtcacctacg cctccatgct ctccctcctc tccctctgcc cgcccttcgt    180
catcctcctg tggtacacga tggtgcacgc ggacggatcc gtggtgcggg cgtacgagca    240
cctccgcgag cacggggtgc tggagggggct caaggccatc tggcccatgc caaccatggc    300
cgcctggaag atatcttcgg ttcggcctct tcgaggccgc gctgcagttc tcctccccgg    360
ggaacgcttc gaagggcccg tctccctcc nggcaagtgc ccgtctacaa aggcaaatgg    420
cttacaanca tatgcaatga cctttgataa atacctganc tgtggtgggt ttggattttt    480
aacctgcaat antatacgat cactnggggg aaatatatcc gccctgtatt tgg           533
```

<210> SEQ ID NO 4
<211> LENGTH: 67
<212> TYPE: PRT
<213> ORGANISM: Oryza sativa

<400> SEQUENCE: 4

```
Lys Thr Val His Ser Ala Leu Val Thr Tyr Ala Ser Met Leu Ser Leu
 1               5                  10                  15
Leu Ser Leu Cys Pro Pro Phe Val Ile Leu Leu Trp Tyr Thr Met Val
             20                  25                  30
His Ala Asp Gly Ser Val Val Arg Ala Tyr Glu His Leu Arg Glu His
         35                  40                  45
Gly Leu Glu Gly Leu Lys Ala Ile Trp Pro Met Pro Thr Met Ala Ala
     50                  55                  60
Trp Lys Ile
 65
```

<210> SEQ ID NO 5
<211> LENGTH: 587
<212> TYPE: DNA
<213> ORGANISM: Glycine max
<220> FEATURE:
<221> NAME/KEY: unsure

```
<222> LOCATION: (282)
<223> OTHER INFORMATION: n = A, C, G, or T
<220> FEATURE:
<221> NAME/KEY: unsure
<222> LOCATION: (335)
<223> OTHER INFORMATION: n = A, C, G, or T
<220> FEATURE:
<221> NAME/KEY: unsure
<222> LOCATION: (355)
<223> OTHER INFORMATION: n = A, C, G, or T
<220> FEATURE:
<221> NAME/KEY: unsure
<222> LOCATION: (525)
<223> OTHER INFORMATION: n = A, C, G, or T
<220> FEATURE:
<221> NAME/KEY: unsure
<222> LOCATION: (530)
<223> OTHER INFORMATION: n = A, C, G, or T

<400> SEQUENCE: 5
catttgcaga gagagagaga gagagagagg gaagacggtt gtggggattc gatgggggcc      60
accgttcact cgccgctagt cacttatgct tccgtcatat ctctgcttac actctgtcct     120
ccgtttgtca tacttctatg gtacaccatg actcttgctg acggatctgt ttccagaca      180 ttccattatt taaggcagaa tgggttgcag ggtttgctac atatatggcc cacccccact     240
cccaccgcct gcaaaatcat tgcagtctat gctgcatttg angcagcact tcagcttctt     300
cttcccgggg aaaaccgttt acggccctat tctcnaaccg gcaaccgact ttctnaaaag     360
gcaaatggtc gcaaagccta ttttgtcacc ttgattactt attttgctct ctggtggttt     420
gggatattca accctacgat tgtttatcat catttgggag aaatttattc aactcccatc     480
ttcggcaact ttctcttctg tgttttcctg tacatcaagg gtcanttggn accgtctcta     540
cagattcggc caactggaaa ttatcatgat tttaggggg atggaat                    587

<210> SEQ ID NO 6
<211> LENGTH: 161
<212> TYPE: PRT
<213> ORGANISM: Glycine max
<220> FEATURE:
<221> NAME/KEY: UNSURE
<222> LOCATION: (77)
<223> OTHER INFORMATION: Xaa = ANY AMINO ACID
<220> FEATURE:
<221> NAME/KEY: UNSURE
<222> LOCATION: (95)
<223> OTHER INFORMATION: Xaa = ANY AMINO ACID
<220> FEATURE:
<221> NAME/KEY: UNSURE
<222> LOCATION: (102)
<223> OTHER INFORMATION: Xaa = ANY AMINO ACID
<220> FEATURE:
<221> NAME/KEY: UNSURE
<222> LOCATION: (157)
<223> OTHER INFORMATION: Xaa = ANY AMINO ACID
<220> FEATURE:
<221> NAME/KEY: UNSURE
<222> LOCATION: (159)
<223> OTHER INFORMATION: Xaa = ANY AMINO ACID

<400> SEQUENCE: 6

Met Gly Ala Thr Val His Ser Pro Leu Val Thr Tyr Ala Ser Val Ile
 1               5                  10                  15

Ser Leu Leu Thr Leu Cys Pro Pro Phe Val Ile Leu Trp Tyr Thr
            20                  25                  30

Met Thr Leu Ala Asp Gly Ser Val Ser Glu Thr Phe His Tyr Leu Arg
        35                  40                  45

Gln Asn Gly Leu Gln Gly Leu Leu His Ile Trp Pro Thr Pro Thr Pro
```

-continued

```
              50                  55                  60
Thr Ala Cys Lys Ile Ile Ala Val Tyr Ala Ala Phe Xaa Ala Ala Leu
 65                  70                  75                  80

Gln Leu Leu Leu Pro Gly Glu Asn Arg Leu Arg Pro Tyr Ser Xaa Thr
                 85                  90                  95

Gly Asn Arg Leu Ser Xaa Lys Ala Asn Gly Arg Lys Ala Tyr Phe Val
                100                 105                 110

Thr Leu Ile Thr Tyr Phe Ala Trp Trp Phe Gly Ile Phe Asn Pro Thr
            115                 120                 125

Ile Val Tyr His His Leu Gly Glu Ile Tyr Ser Thr Pro Ile Phe Gly
130                 135                 140

Asn Phe Leu Phe Cys Val Phe Leu Tyr Ile Lys Gly Xaa Leu Xaa Pro
145                 150                 155                 160

Ser
```

<210> SEQ ID NO 7
<211> LENGTH: 527
<212> TYPE: DNA
<213> ORGANISM: Triticum aestivum
<220> FEATURE:
<221> NAME/KEY: unsure
<222> LOCATION: (99)
<223> OTHER INFORMATION: n = A, C, G, or T
<220> FEATURE:
<221> NAME/KEY: unsure
<222> LOCATION: (497)
<223> OTHER INFORMATION: n = A, C, G, or T

<400> SEQUENCE: 7

```
gctgctgctc ctctcctccc atctcaccac acaccgcagc cccagcaaga tcgcgcggag      60
gccatggcga accaagcctt cctccgccgg cgccaagcna accgcggctg cgccaccggt     120
tacagtgcac tcggcgctgg tcacctacac ctccatgctc gcgctcctct ccctctgccc     180
gcccttcgtc atcctcctgt ggtacacgat ggtgcacgcg gacggatcgg tggtgcggac     240
ttacgagcac ctcagggatc acggcgtgct cgagggctc aaggccatct ggcccatgcc     300
caccctcgtc gcgtggaaga tcatcttcgg cttcgggctc ttcgaggccg tcctacagct     360
gctgctccct gggaagcgct tcgaaggggcc catctcgcct gccgggaacg tgccggtcta     420
caaggcaaat ggcttacaag catatgcagt gaaccttgat aacttacctt ggtttgtggt     480
ggttcggtat atttaancct gcaatagtgt atgatcactt tggggag                   527
```

<210> SEQ ID NO 8
<211> LENGTH: 134
<212> TYPE: PRT
<213> ORGANISM: Triticum aestivum
<220> FEATURE:
<221> NAME/KEY: UNSURE
<222> LOCATION: (124)
<223> OTHER INFORMATION: Xaa = ANY AMINO ACID

<400> SEQUENCE: 8

```
Thr Val His Ser Ala Leu Val Thr Tyr Thr Ser Met Leu Ala Leu Leu
  1               5                  10                  15

Ser Leu Cys Pro Pro Phe Val Ile Leu Leu Trp Tyr Thr Met Val His
                 20                  25                  30

Ala Asp Gly Ser Val Val Arg Thr Tyr Glu His Leu Arg Asp His Gly
             35                  40                  45

Leu Glu Gly Leu Lys Ala Ile Trp Pro Met Pro Thr Leu Val Ala Trp
 50                  55                  60
```

```
Lys Ile Ile Phe Gly Phe Gly Leu Phe Glu Ala Val Leu Gln Leu Leu
 65                  70                  75                  80

Leu Pro Gly Lys Arg Phe Glu Gly Pro Ile Ser Pro Ala Gly Asn Val
                 85                  90                  95

Pro Val Tyr Lys Ala Asn Gly Leu Gln Ala Tyr Ala Val Thr Leu Ile
            100                 105                 110

Thr Tyr Leu Gly Leu Trp Trp Phe Gly Ile Phe Xaa Pro Ala Ile Val
        115                 120                 125

Tyr Asp His Phe Gly Glu
    130
```

<210> SEQ ID NO 9
<211> LENGTH: 1070
<212> TYPE: DNA
<213> ORGANISM: Zea mays
<220> FEATURE:
<221> NAME/KEY: unsure
<222> LOCATION: (885)..(886)
<223> OTHER INFORMATION: n = A, C, G, or T
<220> FEATURE:
<221> NAME/KEY: unsure
<222> LOCATION: (949)
<223> OTHER INFORMATION: n = A, C, G, or T
<220> FEATURE:
<221> NAME/KEY: unsure
<222> LOCATION: (1019)
<223> OTHER INFORMATION: n = A, C, G, or T
<220> FEATURE:
<221> NAME/KEY: unsure
<222> LOCATION: (1050)..(1051)
<223> OTHER INFORMATION: n = A, C, G, or T
<220> FEATURE:
<221> NAME/KEY: unsure
<222> LOCATION: (1058)
<223> OTHER INFORMATION: n = A, C, G, or T

<400> SEQUENCE: 9

```
gcacgagccg cggcacaggc gcacagcggt gcctgccctg cccacacggc cacaccacca      60
cagatccatt ttaaaacccc aggcgtctct cacgcttccg ccgctttaca actccccacc     120
ccagccgatc ccaacgcaca ctgcacccag tgcggcggcc gccggcaatg gcggtgcacg     180
gcggcgacta cctgcggcgg ttcgttgctg agacggagtg gtacaacgag gtcgtcctca     240
gcgccgtggc gccaggcgac tggtggcgcg gcctgccgca cccggtgcag tcgtggatgc     300
gcaactgcgt cggcggttac ctcctctact tcatctctgg tttcctctgg tgtttcgtca     360
tctactactg gaagcgccac gcctacatcc ccaaagatgc catccccaca aatgaagcta     420
tgaagaagca aatagctgta gcatccaagg ctatgccttt ttactgtgct cttccaactt     480
tatctgagta tatgatcgag agtggatgga cccggtgtta ctttaatatc agcgaaatgg     540
gttttttctg cataccttgt tatatggcta tgtatctcat ttttgtggag tttggaattt     600
actggatgca cagagagttg catgacataa agccactata caaacatctg catgcgaccc     660
accatattta caacaaggag aacaccttgt ctccgtttgc tggactcgcg tttcacccac     720
tggatggtat tctgcaagcg ataccgcatg tgcttgcgct cttcctcctc ccaacgcact     780
tcaggacgca catcgctctc gtgttcttgg agggcgtgtg gacgacaaac atccacgact     840
gcattcacgg caaggtatgg ccagtcatgg gcgctgggta tcacnnacat ccacatacga     900
ctttacgcca caactatggg cactacaccg tctggatgga ctggatgtnt ggtacgctcc     960
gtgagccaga tgtatccct caagaagggc tgagtcgtcg tagctgtggt tttcctacng    1020
tgctggatgt gcttggtcgg tccgtccaan ntgctctntc cgctgagcgg               1070
```

<210> SEQ ID NO 10
<211> LENGTH: 260
<212> TYPE: PRT
<213> ORGANISM: Zea mays
<220> FEATURE:
<221> NAME/KEY: UNSURE
<222> LOCATION: (233)
<223> OTHER INFORMATION: Xaa = ANY AMINO ACID
<220> FEATURE:
<221> NAME/KEY: UNSURE
<222> LOCATION: (254)
<223> OTHER INFORMATION: Xaa = ANY AMINO ACID

<400> SEQUENCE: 10

```
Tyr Leu Arg Arg Phe Val Ala Glu Thr Glu Trp Tyr Asn Glu Val Val
  1               5                  10                  15

Leu Ser Ala Val Ala Pro Gly Asp Trp Trp Arg Gly Leu Pro His Pro
             20                  25                  30

Val Gln Ser Trp Met Arg Asn Cys Val Gly Gly Tyr Leu Leu Tyr Phe
         35                  40                  45

Ile Ser Gly Phe Leu Trp Cys Phe Val Ile Tyr Tyr Trp Lys Arg His
 50                  55                  60

Ala Tyr Ile Pro Lys Asp Ala Ile Pro Thr Asn Glu Ala Met Lys Lys
 65                  70                  75                  80

Gln Ile Ala Val Ala Ser Lys Ala Met Pro Phe Tyr Cys Ala Leu Pro
                 85                  90                  95

Thr Leu Ser Glu Tyr Met Ile Glu Ser Gly Trp Thr Arg Cys Tyr Phe
            100                 105                 110

Asn Ile Ser Glu Met Gly Phe Ser Ala Tyr Leu Cys Tyr Met Ala Met
            115                 120                 125

Tyr Leu Ile Phe Val Glu Phe Gly Ile Tyr Trp Met His Arg Glu Leu
130                 135                 140

His Asp Ile Lys Pro Leu Tyr Lys His Leu His Ala Thr His His Ile
145                 150                 155                 160

Tyr Asn Lys Glu Asn Thr Leu Ser Pro Phe Ala Gly Leu Ala Phe His
                165                 170                 175

Pro Leu Asp Gly Ile Leu Gln Ala Ile Pro His Val Leu Ala Leu Phe
            180                 185                 190

Leu Leu Pro Thr His Phe Arg Thr His Ile Ala Leu Val Phe Leu Glu
        195                 200                 205

Gly Val Trp Thr Thr Asn Ile His Asp Cys Ile His Gly Lys Val Trp
210                 215                 220

Pro Val Met Gly Ala Gly Tyr His Xaa His Pro His Thr Thr Leu Arg
225                 230                 235                 240

His Asn Tyr Gly His Tyr Thr Val Trp Met Asp Trp Met Xaa Gly Thr
                245                 250                 255

Leu Arg Glu Pro
            260
```

<210> SEQ ID NO 11
<211> LENGTH: 360
<212> TYPE: DNA
<213> ORGANISM: Oryza sativa

<400> SEQUENCE: 11

```
atcactccac aaacgaaggt tgggtctccc tactctctct ctccacgctt tacaactcaa      60
cccccgcacc accaccagtc caccaccaca atcccagggc ggcgccgcgg ccggcaatgg     120
```

-continued

```
cgggcggcgg cggcgagtac ctgcgccagt tcgtcgagga cacggcctgg tacaacgaga    180
tcttcctcag ccatgtggtc ccgggcgact ggtggcgcgc cctcccccac ccgctccagt    240
cgtggctccg caacggtctc ggtggctacc tcatctactt cgcctgcggg cttcctctgg    300
tgcttcgtca tctaactact ggaagcgcca agcctacatc cccaaaagat tctataccta    360
```

<210> SEQ ID NO 12
<211> LENGTH: 58
<212> TYPE: PRT
<213> ORGANISM: Oryza sativa

<400> SEQUENCE: 12

```
Tyr Leu Arg Gln Phe Val Glu Glu Thr Ala Trp Tyr Asn Glu Ile Phe
 1               5                  10                  15

Leu Ser His Val Val Pro Gly Asp Trp Trp Arg Ala Leu Pro His Pro
            20                  25                  30

Leu Gln Ser Trp Leu Arg Asn Gly Leu Gly Gly Tyr Leu Ile Tyr Phe
        35                  40                  45

Ala Ala Gly Phe Leu Trp Cys Phe Val Ile
    50                  55
```

<210> SEQ ID NO 13
<211> LENGTH: 459
<212> TYPE: DNA
<213> ORGANISM: Glycine max

<400> SEQUENCE: 13

```
ctcgtgccga attcggcacg agtctctctc actattcctt ttcttctcca cggttacttt     60
cggtggatga tggaggaccc cgacaacgttg ttgaacagcg aatattcgag gctgttcggc    120
gaagacacgg acttgtacaa ccgcattgtg ttgggcgccc tattgccgca ctctgtgtgg    180
ggcccactcc cgcgcttcct ccagacgtgg cttcgcaatt acctcggcgg cgttctcctc    240
tacctcctct ctgggctctt gtggtgcttc tacatttatt attgggaagc gcaacgttca    300
tgtccccaaa gatgctattc cctctcaaaa gagcatgctc ttgcaaatat ctgttgctat    360
gaaagccatg ccgtgggtac ctttacttcc aactgtttcc ggatactggg taaaaactgg    420
ctggacaaat gctatcctag attatataat gttgggtgg                            459
```

<210> SEQ ID NO 14
<211> LENGTH: 63
<212> TYPE: PRT
<213> ORGANISM: Glycine max

<400> SEQUENCE: 14

```
Asn Ser Glu Tyr Ser Arg Leu Phe Gly Glu Asp Thr Asp Leu Tyr Asn
 1               5                  10                  15

Arg Ile Val Leu Gly Ala Leu Leu Pro His Ser Val Trp Gly Pro Leu
            20                  25                  30

Pro Arg Phe Leu Gln Thr Trp Leu Arg Asn Tyr Leu Gly Gly Val Leu
        35                  40                  45

Leu Tyr Leu Leu Ser Gly Leu Leu Trp Cys Phe Tyr Ile Tyr Tyr
    50                  55                  60
```

<210> SEQ ID NO 15
<211> LENGTH: 495
<212> TYPE: DNA
<213> ORGANISM: Triticum aestivum
<220> FEATURE:

```
<221> NAME/KEY: unsure
<222> LOCATION: (261)
<223> OTHER INFORMATION: n = A, C, G, or T
<220> FEATURE:
<221> NAME/KEY: unsure
<222> LOCATION: (286)
<223> OTHER INFORMATION: n = A, C, G, or T
<220> FEATURE:
<221> NAME/KEY: unsure
<222> LOCATION: (288)
<223> OTHER INFORMATION: n = A, C, G, or T
<220> FEATURE:
<221> NAME/KEY: unsure
<222> LOCATION: (328)
<223> OTHER INFORMATION: n = A, C, G, or T
<220> FEATURE:
<221> NAME/KEY: unsure
<222> LOCATION: (344)
<223> OTHER INFORMATION: n = A, C, G, or T
<220> FEATURE:
<221> NAME/KEY: unsure
<222> LOCATION: (372)
<223> OTHER INFORMATION: n = A, C, G, or T
<220> FEATURE:
<221> NAME/KEY: unsure
<222> LOCATION: (390)..(391)
<223> OTHER INFORMATION: n = A, C, G, or T
<220> FEATURE:
<221> NAME/KEY: unsure
<222> LOCATION: (450)..(451)
<223> OTHER INFORMATION: n = A, C, G, or T
<220> FEATURE:
<221> NAME/KEY: unsure
<222> LOCATION: (480)
<223> OTHER INFORMATION: n = A, C, G, or T
<220> FEATURE:
<221> NAME/KEY: unsure
<222> LOCATION: (489)
<223> OTHER INFORMATION: n = A, C, G, or T

<400> SEQUENCE: 15
gtacaacgag atcttcctca gcgccgtcgt gccgggcggc ggcggctggt ggcgggcgct      60
gccgcacccg ctccgctcct ggctgcgcaa ctgcatcggc ggctacctcc tctacttcgc     120
caccggcttc ctctggtgct tcgtcatcta ctactggaag cgcaacgcct acatccccaa     180
agatgctgtc cctacagtag aagctatgaa gaagcaaata attgttgcat caaaggctat     240
gcctttctac tgtgctcttc ngtccgtatc tgagcacatg attganantg ggatggacac     300 ggtgttttcct tcaaaacagc aagttggntg gctatgtaca ttanctatgt gtctctatat     360
ctcatctttg tngagttcgg aattaactgn ntgcacagag atttgatgac ataaagccac     420
tatacaagca cctcatcaac caacacattn naacaaggga atacctatca cattgctgan     480
caacatcanc attgg                                                      495

<210> SEQ ID NO 16
<211> LENGTH: 95
<212> TYPE: PRT
<213> ORGANISM: Triticum aestivum
<220> FEATURE:
<221> NAME/KEY: UNSURE
<222> LOCATION: (71)
<223> OTHER INFORMATION: Xaa = ANY AMINO ACID
<220> FEATURE:
<221> NAME/KEY: UNSURE
<222> LOCATION: (79)..(80)
<223> OTHER INFORMATION: Xaa = ANY AMINO ACID

<400> SEQUENCE: 16

Trp Arg Ala Leu Pro His Pro Leu Arg Ser Trp Leu Arg Asn Cys Ile
 1               5                  10                  15
```

Gly Gly Tyr Leu Leu Tyr Phe Ala Thr Gly Phe Leu Trp Cys Phe Val
            20                  25                  30

Ile Tyr Tyr Trp Lys Arg Asn Ala Tyr Ile Pro Lys Asp Ala Val Pro
        35                  40                  45

Thr Val Glu Ala Met Lys Lys Gln Ile Ile Val Ala Ser Lys Ala Met
    50                  55                  60

Pro Phe Tyr Cys Ala Leu Xaa Ser Val Ser Glu His Met Ile Xaa Xaa
65                  70                  75                  80

Gly Met Asp Thr Val Phe Pro Ser Lys Gln Gln Val Gly Trp Leu
                85                  90                  95

<210> SEQ ID NO 17
<211> LENGTH: 1870
<212> TYPE: DNA
<213> ORGANISM: Oryza sativa

<400> SEQUENCE: 17

| | | | | | |
|---|---|---|---|---|---|
| gcacgagctt | acactcactc | gatctccttc | ctccactgtc | gctcagatcg | acgcgggcca | 60 |
| tggccaagcc | tagggcctcc | gccgccgcgg | cgaaggcgcc | agcctccacg | ccgcccaaga | 120 |
| cggtgcactc | ggcgctcgtc | acctacgcct | ccatgctctc | cctcctctcc | ctctgcccgc | 180 |
| ccttcgtcat | cctcctgtgg | tacacgatgg | tgcacgcgga | cggatccgtg | gtgcgggcgt | 240 |
| acgagcacct | ccgcgagcac | ggggtgctgg | agggggctcaa | ggccatctgg | cccatgccaa | 300 |
| ccatggccgc | ctggaagatc | atcttcggct | tcggcctctt | cgaggccgcg | ctgcagcttc | 360 |
| tcctccccgg | gaagcgcttc | gagggccccg | tctcccccctc | gggcaacgtg | cccgtctaca | 420 |
| aggcaaatgg | cttacaagca | tatgcagtga | ccttgataac | atacctgagc | ctgtggtggt | 480 |
| ttggaatttt | taaccctgca | atagtatacg | atcacttggg | ggaaatatac | tctgctcttg | 540 |
| tatttggaag | ctttgtgttc | tgtattttc | tgtacataaa | gggtcatctt | gctccatctt | 600 |
| catctgattc | tggatcctca | gggaatgtga | taattgattt | ctactgggga | atggaactat | 660 |
| atcctcgcat | tggtaagcac | tttgatatca | agtgttcac | aaactgccgt | tttgggatga | 720 |
| tgtcctgggc | tgttcttgct | gtaacctact | gcataaagca | gtatgaaatg | aatggccgag | 780 |
| ttgcagattc | aatgcttgtg | aatactgcat | tgatgttgat | ctatgtcacc | aagttcttct | 840 |
| ggtgggaatc | tggatactgg | tgcactatgg | acattgctca | tgatagagct | ggtttctaca | 900 |
| tttgctgggg | atgcttggta | tgggttccat | caatatacac | ctctcctgga | atgtaccttg | 960 |
| tcaaccaccc | tgtgaatttg | gtccccagc | tagcactctc | aattctcctt | gctggaatat | 1020 |
| tgtgcatata | tataaactat | gactgtgatc | gtcagcgcca | agaattccgt | cggacaaatg | 1080 |
| ggaaatgctc | aatatggggc | aaagctccat | ctaagattgt | tgcttcctat | cagactacaa | 1140 |
| atggagaaac | aaaaagcagt | cttctcttga | cttctggatg | gtgggggcttg | tctcgtcatt | 1200 |
| ttcactatgt | tccagagatt | ctatctgctt | ttttctggac | agttccagct | ctttttgatc | 1260 |
| atttcctgcc | gtacttctat | gtgatctttc | tgaccatatt | gctgttcgac | cgagctaaaa | 1320 |
| gggatgatga | ccgatgctca | tcaaagtatg | gcaagtattg | gaagatgtac | tgcaacaaag | 1380 |
| taccgtgcag | ggttattcct | ggcatttact | gaggttgttg | accatgttca | acaacttctc | 1440 |
| gggataaaac | tcagccatgt | tgtgaattcc | tttctctggg | acgatctact | gctgtttgtg | 1500 |
| taatatgtca | ttagcttgat | gtatgcagga | ttagattcgg | gctgattggt | ttcaaccttt | 1560 |
| tgagtttgct | gtatccaacc | ctgacacaga | tgagtcaacg | atgccgccaa | atcgtgatt | 1620 |
| ttcttgttag | ctcgctgata | ggagagatga | ttgcaggatc | atagtttgtg | tagtttgtac | 1680 |

-continued

```
cttataatgg atgtttcgac ttcatttttc tgctagaagc gattaggcag cacgaaaatg    1740
aaattgtttg aggttctgta ctgctcgaat aatgttgctg caactgtatt atccatgaac    1800
tgtaataatt caaagtttgg caacaggcat ggtgattggt tctacacatt ttaaaaaaaa    1860
aaaaaaaaaa                                                          1870
```

<210> SEQ ID NO 18
<211> LENGTH: 430
<212> TYPE: PRT
<213> ORGANISM: Oryza sativa

<400> SEQUENCE: 18

```
Lys Thr Val His Ser Ala Leu Val Thr Tyr Ala Ser Met Leu Ser Leu
 1               5                  10                  15

Leu Ser Leu Cys Pro Pro Phe Val Ile Leu Leu Trp Tyr Thr Met Val
            20                  25                  30

His Ala Asp Gly Ser Val Val Arg Ala Tyr Glu His Leu Arg Glu His
        35                  40                  45

Gly Leu Glu Gly Leu Lys Ala Ile Trp Pro Met Pro Thr Met Ala Ala
    50                  55                  60

Trp Lys Ile Ile Phe Gly Phe Gly Leu Phe Glu Ala Ala Leu Gln Leu
65                  70                  75                  80

Leu Leu Pro Gly Lys Arg Phe Glu Gly Pro Val Ser Pro Ser Gly Asn
                85                  90                  95

Val Pro Val Tyr Lys Ala Asn Gly Leu Gln Ala Tyr Ala Val Thr Leu
           100                 105                 110

Ile Thr Tyr Leu Ser Leu Trp Trp Phe Gly Ile Phe Asn Pro Ala Ile
       115                 120                 125

Val Tyr Asp His Leu Gly Glu Ile Tyr Ser Ala Leu Val Phe Gly Ser
   130                 135                 140

Phe Val Phe Cys Ile Phe Leu Tyr Ile Lys Gly His Leu Ala Pro Ser
145                 150                 155                 160

Ser Ser Asp Ser Gly Ser Ser Gly Asn Val Ile Ile Asp Phe Tyr Trp
                165                 170                 175

Gly Met Glu Leu Tyr Pro Arg Ile Gly Lys His Phe Asp Ile Lys Val
           180                 185                 190

Phe Thr Asn Cys Arg Phe Gly Met Met Ser Trp Ala Val Leu Ala Val
       195                 200                 205

Thr Tyr Cys Ile Lys Gln Tyr Glu Met Asn Gly Arg Val Ala Asp Ser
   210                 215                 220

Met Leu Val Asn Thr Ala Leu Met Leu Ile Tyr Val Thr Lys Phe Phe
225                 230                 235                 240

Trp Trp Glu Ser Gly Tyr Trp Cys Thr Met Asp Ile Ala His Asp Arg
                245                 250                 255

Ala Gly Phe Tyr Ile Cys Trp Gly Cys Leu Val Trp Val Pro Ser Ile
           260                 265                 270

Tyr Thr Ser Pro Gly Met Tyr Leu Val Asn His Pro Val Asn Leu Gly
       275                 280                 285

Pro Gln Leu Ala Leu Ser Ile Leu Leu Ala Gly Ile Leu Cys Ile Tyr
   290                 295                 300

Ile Asn Tyr Asp Cys Asp Arg Gln Arg Gln Glu Phe Arg Arg Thr Asn
305                 310                 315                 320

Gly Lys Cys Ser Ile Trp Gly Lys Ala Pro Ser Lys Ile Val Ala Ser
                325                 330                 335
```

| | | | | | | | | | | | |
|---|---|---|---|---|---|---|---|---|---|---|---|
|Tyr|Gln|Thr|Thr|Asn|Gly|Glu|Thr|Lys|Ser|Ser|Leu|Leu|Thr|Ser|
| | | |340| | | |345| | | |350| | | |

Gly Trp Trp Gly Leu Ser Arg His Phe His Tyr Val Pro Glu Ile Leu
             355                 360               365

Ser Ala Phe Phe Trp Thr Val Pro Ala Leu Phe Asp His Phe Leu Pro
370                     375                    380

Tyr Phe Tyr Val Ile Phe Leu Thr Ile Leu Leu Phe Asp Arg Ala Lys
385                     390                    395                 400

Arg Asp Asp Asp Arg Cys Ser Ser Lys Tyr Gly Lys Tyr Trp Lys Met
             405                 410                 415

Tyr Cys Asn Lys Val Pro Cys Arg Val Ile Pro Gly Ile Tyr
             420                 425                 430

<210> SEQ ID NO 19
<211> LENGTH: 1646
<212> TYPE: DNA
<213> ORGANISM: Glycine max

<400> SEQUENCE: 19

```
gcacgagcat tgcagagag  agagagagag agagagggaa gacggttgtg gggattcgat    60
gggggccacc gttcactcgc cgctagtcac ttatgcttcc gtcatatctc tgcttacact   120
ctgtcctccg tttgtcatac ttctatggta caccatgact cttgctgacg gatctgtttc   180
cgagacattc cattatttaa ggcagaatgg gttgcagggt ttgctacata tatggcccac   240
ccccactccc accgcctgca aaatcattgc agtctatgct gcatttgagg cagcacttca   300
gcttcttctt cccgggaaaa ccgtttacgg ccctatttct ccaaccggcc accgacctgt   360
ctacaaggca aatggtctgc aagcctattt tgtcaccttg attacttatt ttgctctctg   420
gtggtttggg atattcaacc ctacgattgt ttatcatcat ttgggagaaa tttattcagc   480
tctcatcttc ggcagctttc tcttctgtgt tttcttgtac atcaagggtc atttggcacc   540
gtcttctaca gattctggct catctggaaa cttaatcatt gattttact  ggggatgga   600
acttatcca cgcattggaa acatttttga cataaaagtc ttcacaaact gcagatttgg   660
aatgatgtca tgggctgttc ttgcactgac ctactgcata aagcagtatg aagaaaatgg   720
aaaagtagcg gactcaatgc ttgtaaatac tgcattaatg ctggtatatg ttaccaagtt   780
tttctggtgg gaagctggat attggagcac aatggatatt gcacatgatc gagctggatt   840
ttatatttgc tggggttgct tggtgtgggt tccatctgtt tatacgtctc ctggaatgta   900
ccttgtcaac catcctgtaa atcttggcat caagctagcg ctctcaattt tagtagctgg   960
cattctttgc atatacatca actatgattg tgacaggcaa aggcaagaat tcgtaggac   1020
aaatggaaaa ggcacagtct ggggaaaagc tccttcaaag atagaggcca catatactac  1080
tacttctggg gaaactaaaa gaagccttct tttaacctct ggatggtggg gattatctcg  1140
tcactttcat tatgtccctg aaatactggc agctttcttc tggacagtcc cagctctttt  1200
cgaacatttt ttgccttact tctacgtgat atttcttacc atccttctct tgatcgagc   1260
aaaacgagat gatgatcgtt gcagatccaa gtatggcaag tactgaaaac tatattgcga  1320
caaggtacct tacagaatca ttccaggaat atactgaaga atgattatcg aaaacggctt  1380
atctggagtc ccccaactta aaattaaaaa ccaaggacgc catctgtagc tttatattgt  1440
ttggtgcctc cttaagacac gtggtagatt agactttcgc tgagagctaa ttattgaatt  1500
attgaaccgg atttttaag  ctaatgtcga gacttgattt cggctccagc tgtgttaatc  1560
tctttatcta tgacttgtga gaaaggtgca tggtttacgg gctggtgtta caaaaaaaaa  1620
```

-continued

```
aaaaaaaaaa aaaaaaaaaa aaaaaa                                      1646

<210> SEQ ID NO 20
<211> LENGTH: 432
<212> TYPE: PRT
<213> ORGANISM: Glycine max

<400> SEQUENCE: 20

Met Gly Ala Thr Val His Ser Pro Leu Val Thr Tyr Ala Ser Val Ile
 1               5                  10                  15

Ser Leu Leu Thr Leu Cys Pro Pro Phe Val Ile Leu Leu Trp Tyr Thr
            20                  25                  30

Met Thr Leu Ala Asp Gly Ser Val Ser Glu Thr Phe His Tyr Leu Arg
        35                  40                  45

Gln Asn Gly Leu Gln Gly Leu Leu His Ile Trp Pro Thr Pro Thr Pro
    50                  55                  60

Thr Ala Cys Lys Ile Ile Ala Val Tyr Ala Ala Phe Glu Ala Ala Leu
65                  70                  75                  80

Gln Leu Leu Leu Pro Gly Lys Thr Val Tyr Gly Pro Ile Ser Pro Thr
                85                  90                  95

Gly His Arg Pro Val Tyr Lys Ala Asn Gly Leu Gln Ala Tyr Phe Val
            100                 105                 110

Thr Leu Ile Thr Tyr Phe Ala Leu Trp Trp Phe Gly Ile Phe Asn Pro
        115                 120                 125

Thr Ile Val Tyr His His Leu Gly Glu Ile Tyr Ser Ala Leu Ile Phe
    130                 135                 140

Gly Ser Phe Leu Phe Cys Val Phe Leu Tyr Ile Lys Gly His Leu Ala
145                 150                 155                 160

Pro Ser Ser Thr Asp Ser Gly Ser Gly Asn Leu Ile Ile Asp Phe
                165                 170                 175

Tyr Trp Gly Met Glu Leu Tyr Pro Arg Ile Gly Lys His Phe Asp Ile
            180                 185                 190

Lys Val Phe Thr Asn Cys Arg Phe Gly Met Met Ser Trp Ala Val Leu
        195                 200                 205

Ala Leu Thr Tyr Cys Ile Lys Gln Tyr Glu Glu Asn Gly Lys Val Ala
    210                 215                 220

Asp Ser Met Leu Val Asn Thr Ala Leu Met Leu Val Tyr Val Thr Lys
225                 230                 235                 240

Phe Phe Trp Trp Glu Ala Gly Tyr Trp Ser Thr Met Asp Ile Ala His
                245                 250                 255

Asp Arg Ala Gly Phe Tyr Ile Cys Trp Gly Cys Leu Val Trp Val Pro
            260                 265                 270

Ser Val Tyr Thr Ser Pro Gly Met Tyr Leu Val Asn His Pro Val Asn
        275                 280                 285

Leu Gly Ile Lys Leu Ala Leu Ser Ile Leu Val Ala Gly Ile Leu Cys
    290                 295                 300

Ile Tyr Ile Asn Tyr Asp Cys Asp Arg Gln Arg Gln Glu Phe Arg Arg
305                 310                 315                 320

Thr Asn Gly Lys Gly Thr Val Trp Gly Lys Ala Pro Ser Lys Ile Glu
                325                 330                 335

Ala Thr Tyr Thr Thr Thr Ser Gly Glu Thr Lys Arg Ser Leu Leu Leu
            340                 345                 350

Thr Ser Gly Trp Trp Gly Leu Ser Arg His Phe His Tyr Val Pro Glu
        355                 360                 365
```

```
Ile Leu Ala Ala Phe Phe Trp Thr Val Pro Ala Leu Phe Glu His Phe
    370                 375                 380

Leu Pro Tyr Phe Tyr Val Ile Phe Leu Thr Ile Leu Leu Phe Asp Arg
385                 390                 395                 400

Ala Lys Arg Asp Asp Asp Arg Cys Arg Ser Lys Tyr Gly Lys Tyr Trp
                405                 410                 415

Lys Leu Tyr Cys Asp Lys Val Pro Tyr Arg Ile Ile Pro Gly Ile Tyr
            420                 425                 430

<210> SEQ ID NO 21
<211> LENGTH: 1695
<212> TYPE: DNA
<213> ORGANISM: Triticum aestivum

<400> SEQUENCE: 21
gcacgaggct gctgctcctc tcctcccatc tcaccacaca ccgcagcccc agcaagatcg      60
cgcggaggcc atggcgaagc ccaagccttc ctccgccggc gccaagccga ccgcggctgc     120
gccaccggtt acagtgcact cggcgctggt cacctacacc tccatgctcg cgctcctctc     180
cctctgcccg cccttcgtca tcctcctgtg gtacacgatg gtgcacgcgg acggatcggt     240
ggtgcggact tacgagcacc tcagggatca cggcgtgctc gagggggctca aggccatctg     300
gcccatgccc accctcgtcg cgtggaagat catcttcggc ttcgggctct tcgaggccgt     360
cctacagctg ctgctccctg ggaagcgctt cgaagggccc atctcgcctg ccgggaacgt     420
gccggtctac aaggcaaatg gcttacaagc atatgcagtg accttgataa cttaccttgg     480
tttgtggtgg ttcggtatat ttaaccctgc aatagtgtat gatcacttgg gggagatata     540
ctctgctctt gtttttggaa gctttgtgtt ctgtattttt ctctacataa agggccatgt     600
atttccatct tcatctgact ctggatcctc tgggaatgtg ataattgact tctactgggg     660
tatggagctg taccctcgga ttggcaagca ctttgatatc aaagtattca ccaactgtcg     720
tttcggtatg atgtcctggg ctgttcttgc cgtaacctat tgcataaagc agtatgaaat     780
gaatggcaga gttgctgatt ctatgcttgt gaatactgca cttatgttga tctatatcac     840
taagttcttt tggtgggaat ctggatattg gtgtactatg acattgctcc atgatagagc     900
tggtttctat atctgctggg gatgcttggt atgggttcca tccatatata cttcccctgg     960
aatgtacctt gtaaaccacc ctttgaattt gggcccccag ctagcactct caattcttct    1020
agctggaatg ttgtgcatat acataaacta tgattgtgac cgtcagcgcc aagaatttcg    1080
acggacgaat gggaaatgct cggtctgggg caaggctcca tctaagattg ttgcctctta    1140
tcagactaca aagggagaaa ctaaaaccag tcttctcttg acttctggat ggtggggctt    1200
gtcacgtcac ttccactatg tcccagagat actatctgca tttttctgga ctgttccagc    1260
tcttttcaat cacttcctac catacttcta cgtgatcttt ctgactatat tattgtttga    1320
ccgagcaaag agggatgatg accggtgctc atcaaagtac gggaagtact ggaagattta    1380
ctgcaacaaa gtaccataca gagtcattcc tggcatttac tgagcatctc gagttctgga    1440
cgactcttga tattaagctc aacagatgcc acgatatcca gtcttcatac cgatttgcta    1500
ctgattgtgt aatgtcgctg gtaggcttgg gctgtacgca gtattaggtg taggcaactt    1560
ggcttttggc atttaccttg tatgtgtcgt gtatctaggg ctgggcttg ctccttcagt    1620
tgttagacag tagggggtaa tctcaggggt gcaatgtact ccctccgtcc taaaataaaa    1680
gcatatctag tattt                                                    1695
```

-continued

<210> SEQ ID NO 22
<211> LENGTH: 450
<212> TYPE: PRT
<213> ORGANISM: Triticum aestivum

<400> SEQUENCE: 22

| | | | | | | | | | | | | | | |
|---|---|---|---|---|---|---|---|---|---|---|---|---|---|---|
| Met | Ala | Lys | Pro | Lys | Pro | Ser | Ala | Gly | Ala | Lys | Pro | Thr | Ala | Ala |
| 1 | | | | 5 | | | | | 10 | | | | | 15 |
| Ala | Pro | Pro | Val | Thr | Val | His | Ser | Ala | Leu | Val | Thr | Tyr | Thr | Ser | Met |
| | | | 20 | | | | | 25 | | | | | 30 | | |
| Leu | Ala | Leu | Leu | Ser | Leu | Cys | Pro | Pro | Phe | Val | Ile | Leu | Leu | Trp | Tyr |
| | | 35 | | | | | 40 | | | | | 45 | | | |
| Thr | Met | Val | His | Ala | Asp | Gly | Ser | Val | Val | Arg | Thr | Tyr | Glu | His | Leu |
| | 50 | | | | | 55 | | | | | 60 | | | | |
| Arg | Asp | His | Gly | Val | Leu | Glu | Gly | Leu | Lys | Ala | Ile | Trp | Pro | Met | Pro |
| 65 | | | | | 70 | | | | | 75 | | | | | 80 |
| Thr | Leu | Val | Ala | Trp | Lys | Ile | Ile | Phe | Gly | Phe | Gly | Leu | Phe | Glu | Ala |
| | | | | 85 | | | | | 90 | | | | | 95 | |
| Val | Leu | Gln | Leu | Leu | Pro | Gly | Lys | Arg | Phe | Glu | Gly | Pro | Ile | Ser |
| | | | | 100 | | | | | 105 | | | | | 110 | |
| Pro | Ala | Gly | Asn | Val | Pro | Val | Tyr | Lys | Ala | Asn | Gly | Leu | Gln | Ala | Tyr |
| | | | 115 | | | | | 120 | | | | | 125 | | |
| Ala | Val | Thr | Leu | Ile | Thr | Tyr | Leu | Gly | Leu | Trp | Trp | Phe | Gly | Ile | Phe |
| | 130 | | | | | 135 | | | | | 140 | | | | |
| Asn | Pro | Ala | Ile | Val | Tyr | Asp | His | Leu | Gly | Glu | Ile | Tyr | Ser | Ala | Leu |
| 145 | | | | | 150 | | | | | 155 | | | | | 160 |
| Val | Phe | Gly | Ser | Phe | Val | Phe | Cys | Ile | Phe | Leu | Tyr | Ile | Lys | Gly | His |
| | | | | 165 | | | | | 170 | | | | | 175 | |
| Val | Phe | Pro | Ser | Ser | Asp | Ser | Gly | Ser | Ser | Gly | Asn | Val | Ile | Ile |
| | | | | 180 | | | | | 185 | | | | | 190 | |
| Asp | Phe | Tyr | Trp | Gly | Met | Glu | Leu | Tyr | Pro | Arg | Ile | Gly | Lys | His | Phe |
| | | | 195 | | | | | 200 | | | | | 205 | | |
| Asp | Ile | Lys | Val | Phe | Thr | Asn | Cys | Arg | Phe | Gly | Met | Met | Ser | Trp | Ala |
| | 210 | | | | | 215 | | | | | 220 | | | | |
| Val | Leu | Ala | Val | Thr | Tyr | Cys | Ile | Lys | Gln | Tyr | Glu | Met | Asn | Gly | Arg |
| 225 | | | | | 230 | | | | | 235 | | | | | 240 |
| Val | Ala | Asp | Ser | Met | Leu | Val | Asn | Thr | Ala | Leu | Met | Leu | Ile | Tyr | Ile |
| | | | | 245 | | | | | 250 | | | | | 255 | |
| Thr | Lys | Phe | Phe | Trp | Trp | Glu | Ser | Gly | Tyr | Trp | Cys | Thr | Met | Asp | Ile |
| | | | | 260 | | | | | 265 | | | | | 270 | |
| Ala | His | Asp | Arg | Ala | Gly | Phe | Tyr | Ile | Cys | Trp | Gly | Cys | Leu | Val | Trp |
| | | | 275 | | | | | 280 | | | | | 285 | | |
| Val | Pro | Ser | Ile | Tyr | Thr | Ser | Pro | Gly | Met | Tyr | Leu | Val | Asn | His | Pro |
| | 290 | | | | | 295 | | | | | 300 | | | | |
| Leu | Asn | Leu | Gly | Pro | Gln | Leu | Ala | Leu | Ser | Ile | Leu | Leu | Ala | Gly | Met |
| 305 | | | | | 310 | | | | | 315 | | | | | 320 |
| Leu | Cys | Ile | Tyr | Ile | Asn | Tyr | Asp | Cys | Asp | Arg | Gln | Arg | Gln | Glu | Phe |
| | | | | 325 | | | | | 330 | | | | | 335 | |
| Arg | Arg | Thr | Asn | Gly | Lys | Cys | Ser | Val | Trp | Gly | Lys | Ala | Pro | Ser | Lys |
| | | | 340 | | | | | 345 | | | | | 350 | | |
| Ile | Val | Ala | Ser | Tyr | Gln | Thr | Thr | Lys | Gly | Glu | Thr | Lys | Thr | Ser | Leu |
| | 355 | | | | | 360 | | | | | 365 | | | | |
| Leu | Leu | Thr | Ser | Gly | Trp | Trp | Gly | Leu | Ser | Arg | His | Phe | His | Tyr | Val |
| | 370 | | | | | 375 | | | | | 380 | | | | |

```
Pro Glu Ile Leu Ser Ala Phe Phe Trp Thr Val Pro Ala Leu Phe Asn
385                 390                 395                 400

His Phe Leu Pro Tyr Phe Tyr Val Ile Phe Leu Thr Ile Leu Leu Phe
                405                 410                 415

Asp Arg Ala Lys Arg Asp Asp Arg Cys Ser Ser Lys Tyr Gly Lys
                420                 425                 430

Tyr Trp Lys Ile Tyr Cys Asn Lys Val Pro Tyr Arg Val Ile Pro Gly
            435                 440                 445

Ile Tyr
    450
```

<210> SEQ ID NO 23
<211> LENGTH: 911
<212> TYPE: DNA
<213> ORGANISM: Zea mays

<400> SEQUENCE: 23

```
cggacgagag ggaacgtagg ctgtgctcac gcagcctccg tgctcgtatg agtacgggca      60
attcaacgat gccgatgcca tccccacaaa tgaagctatg aagaagcaaa tagctgtagc     120
atccaaggct atgcctttt actgtgctct ccaactttta tctgagtata tgatcgagag     180
tggatggacc cggtgttact ttaatatcag cgaaatgggt ttttctgcat acctttgtta     240
tatggctatg tatctcattt ttgtggagtt tggaattttac tggatgcaca gagagttgca     300
tgacataaag ccactataca acatctgca tgcgacccac catatttaca acaaggagaa     360
caccttgtct ccgtttgctg gactcgcgtt tcacccactg gatggtattc tgcaagcgat     420
accgcatgtg cttgcgctct tcctcctccc aacgcacttc aggacgcaca tcgctctcgt     480
gttcttggag ggcgtgtgga cgacaaacat ccacgactgc attcacggca aggtatggcc     540
agtcatgggc gctgggtatc acaccatcca ccatacgact taccgccaca actatggcca     600
ctacaccgtc tggatggact ggatgtttgg tacgctccgt gagccagatg atatcctcaa     660
gaaggcctga gttcgtcgta gctgtggttt tcctacggtg ctggatgtgc ttggtctgtt     720
ctgtccccag tgcctctaat ccgctgagcc tgttcagcgc tctgtttctg taggctttgg     780
tgtgctattt agtttgctag gttttatatg ttgtgcttat tctgtaattt agtgatgttt     840
gtctcatgac gcaacggagt tcaggacgaa taaaagaaa gatttgctag acaaaaaaaa     900
aaaaaaaaaa a                                                           911
```

<210> SEQ ID NO 24
<211> LENGTH: 191
<212> TYPE: PRT
<213> ORGANISM: Zea mays

<400> SEQUENCE: 24

```
Asp Ala Ile Pro Thr Asn Glu Ala Met Lys Lys Gln Ile Ala Val Ala
1               5                   10                  15

Ser Lys Ala Met Pro Phe Tyr Cys Ala Leu Pro Thr Leu Ser Glu Tyr
            20                  25                  30

Met Ile Glu Ser Gly Trp Thr Arg Cys Tyr Phe Asn Ile Ser Glu Met
        35                  40                  45

Gly Phe Ser Ala Tyr Leu Cys Tyr Met Ala Met Tyr Leu Ile Phe Val
    50                  55                  60

Glu Phe Gly Ile Tyr Trp Met His Arg Glu Leu His Asp Ile Lys Pro
65                  70                  75                  80
```

```
Leu Tyr Lys His Leu His Ala Thr His Ile Tyr Asn Lys Glu Asn
                 85                  90                  95

Thr Leu Ser Pro Phe Ala Gly Leu Ala Phe His Pro Leu Asp Gly Ile
            100                 105                 110

Leu Gln Ala Ile Pro His Val Leu Ala Leu Phe Leu Leu Pro Thr His
        115                 120                 125

Phe Arg Thr His Ile Ala Leu Val Phe Leu Glu Gly Val Trp Thr Thr
130                 135                 140

Asn Ile His Asp Cys Ile His Gly Lys Val Trp Pro Val Met Gly Ala
145                 150                 155                 160

Gly Tyr His Thr Ile His His Thr Thr Tyr Arg His Asn Tyr Gly His
                165                 170                 175

Tyr Thr Val Trp Met Asp Trp Met Phe Gly Thr Leu Arg Glu Pro
            180                 185                 190

<210> SEQ ID NO 25
<211> LENGTH: 1318
<212> TYPE: DNA
<213> ORGANISM: Oryza sativa

<400> SEQUENCE: 25
gcacgagatc actccacaaa cgaaggttgg gtctccctac tctctctctc cacgctttac      60
aactcaaccc ccgcaccacc accagtccac caccacaatc ccagggcggc gccgcggccg     120
gcaatggcgg gcggcggcgg cgagtacctg cgccagttcg tcgaggagac ggcctggtac     180
aacgagatct tcctcagcca tgtggtcccg ggcgactggg gcgcgccct cccccacccg      240 ctccagtcgt ggctccgcaa cggcctcggc ggctacctca tctacttcgc ctgcggcttc     300
ctctggtgct tcgtcatcta ctactggaag cgccacgcct acatcccaa agattctata      360 cctacaatcg aagctatgaa gaagcaaata attgttgcat caaaggctat gcctctctat     420
tgtgcccttc caaccttatc tgagtacatg gttgagaatg gatggacaca gtgttatgtt     480
aatatcagtg aagttggttg gccaatgtac ctggtttatc tggctttata tcttatcttt     540
gttgagtttg gaatttactg gatgcacaga gagttgcatg acataaagcc attgtacaag     600
tacctgcaca cataccacca tatttacaac aaggagaata ccctatcacc atttgcagga    660
ctagcattcc atccactgga tgggattttg caagccatac gcatgtgtt tgcgctctac      720 cttatcccaa cacacttcag gacacacatt gctctcttgt tcatagaggc cgtgtggaca     780
actaacatcc atgactgcat tcacggcaag gtttggccgg tcatgggtgc tggctatcac     840
accattcacc atacaacata ccgtcacaac tatggccact acaccgtgtg gatggactgg     900
atgttcggca cccttcgaga gccagaagat atcttgaaga aggattagga tcgaattgtt     960
aagcacggcg cgacgttcgc ctctcgtctt tgtagcagtc ggaagaaggg ggttctatgt    1020
atttatcctg ctcgatgcta tctgttatct tcatgtacc aatgtgctgt ttcagtatgc     1080
taggtgaaca taaaagtgaa ctttagtgag ttcatcatcc ctggaatgca atggaatcga    1140
gagatatatc ctgggtaggt tccaggtgtt gtaccattc ctgaatttct ctgtacttct     1200
ttgtgtcaaa gaacatgatg aacagttgtg gccagctttt gtacagcaat aactgtttta    1260
ttgtaactgc tgccatcctt ttgtatcaaa aaaaaaaaa aaaaaaaaa aaaaaaa        1318

<210> SEQ ID NO 26
<211> LENGTH: 261
<212> TYPE: PRT
<213> ORGANISM: Oryza sativa
```

```
<400> SEQUENCE: 26

Glu Tyr Leu Arg Gln Phe Val Glu Glu Thr Ala Trp Tyr Asn Glu Ile
  1               5                  10                  15

Phe Leu Ser His Val Val Pro Gly Asp Trp Trp Arg Ala Leu Pro His
                 20                  25                  30

Pro Leu Gln Ser Trp Leu Arg Asn Gly Leu Gly Gly Tyr Leu Ile Tyr
             35                  40                  45

Phe Ala Cys Gly Phe Leu Trp Cys Phe Val Ile Tyr Tyr Trp Lys Arg
         50                  55                  60

His Ala Tyr Ile Pro Lys Asp Ser Ile Pro Thr Ile Glu Ala Met Lys
 65                  70                  75                  80

Lys Gln Ile Ile Val Ala Ser Lys Ala Met Pro Leu Tyr Cys Ala Leu
                 85                  90                  95

Pro Thr Leu Ser Glu Tyr Met Val Glu Asn Gly Trp Thr Gln Cys Tyr
            100                 105                 110

Val Asn Ile Ser Glu Val Gly Trp Pro Met Tyr Leu Val Tyr Leu Ala
        115                 120                 125

Leu Tyr Leu Ile Phe Val Glu Phe Gly Ile Tyr Trp Met His Arg Glu
130                 135                 140

Leu His Asp Ile Lys Pro Leu Tyr Lys Tyr Leu His Thr Tyr His His
145                 150                 155                 160

Ile Tyr Asn Lys Glu Asn Thr Leu Ser Pro Phe Ala Gly Leu Ala Phe
                165                 170                 175

His Pro Leu Asp Gly Ile Leu Gln Ala Ile Pro His Val Phe Ala Leu
            180                 185                 190

Tyr Leu Ile Pro Thr His Phe Arg Thr His Ile Ala Leu Leu Phe Ile
        195                 200                 205

Glu Ala Val Trp Thr Thr Asn Ile His Asp Cys Ile His Gly Lys Val
210                 215                 220

Trp Pro Val Met Gly Ala Gly Tyr His Thr Ile His His Thr Thr Tyr
225                 230                 235                 240

Arg His Asn Tyr Gly His Tyr Thr Val Trp Met Asp Trp Met Phe Gly
                245                 250                 255

Thr Leu Arg Glu Pro
            260

<210> SEQ ID NO 27
<211> LENGTH: 1447
<212> TYPE: DNA
<213> ORGANISM: Glycine max

<400> SEQUENCE: 27
gcacgagctc gtgccgaatt cggcacgagt ctctctcact attccttttc ttctccacgg    60
ttactttcgg tggatgatgg aggacccgac aacgttgttg aacagcgaat attcgaggct   120
gttcggcgaa gacacggact tgtacaaccg cattgtgttg ggcgccctat tgccgcactc   180
tgtgtggggc ccactcccgc gcttcctcca gacgtggctt cgcaattacc tcggcggcgt   240
tctcctctac ctcctctctg ggctcttgtg gtgcttctac atttattatt ggaagcgcaa   300
cgttcatgtc cccaaagatg ctattccctc tcaaagagcc atgctcttgc aaatatctgt   360
tgctatgaaa gccatgccgt ggtactcttt acttccaact gtttcggagt acctggtaga   420
aactggctgg acaaagtgct atcctagatt atataatgtt ggttggcttg cataccttgt   480
gtatttagca atttatctaa ttattgtaga gtttggtatt tattggatgc acagagagct   540
```

```
gcacgacata aaaccgcttt acaaatatct tcatgctacc catcacatct acaataaaca    600
gaacactctc tcccctttg ctggtttggc atttcaccct cttgatggga tacttcaggc     660
attaccgcat agcctttgtt tgttttttat gccaatccat tttactacac atttggccct    720
catattcatt gagggcgttt ggactgcaaa tattcatgat tgcattcatg gaaaattgtg    780
gcctgttatg ggtgctggtt accacaccat tcatcacact acatatcggc acaactacgg    840
ccactacacc atatgatgg attggatgtt tggaactctt cgcgaccccg aggaggatgg     900
gggcaaggcg atgtgatgaa atgcagactt gcactggcag tcattggtta tcatgtttgg    960
attgttgaaa tgtcgttcct tgcatgtata gcataaatgc gtgagctata tttttctgat   1020
gtccatcaca aggtgatgtt ctatattaga gagacaaggt taaagtggag cttccctgtc   1080
tcaaatccca ttgttagtgt atgtggttga ggttattttc tttctcaaat tacgtggtag   1140
agattgagat agtaatgcag ttttctctag atgtgacaat agatggtctc cctattaatg   1200
ctttgttttg tttcattttc tttccttcta tgtttataga ataaaccaca ctctctaagg   1260
gtgtgtttgg ttgtaaagag aaaaagatg ggaatggaag agaataggtg agaagagaaa    1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaa                                                             1447

<210> SEQ ID NO 28
<211> LENGTH: 269
<212> TYPE: PRT
<213> ORGANISM: Glycine max

<400> SEQUENCE: 28

Glu Tyr Ser Arg Leu Phe Gly Glu Asp Thr Asp Leu Tyr Asn Arg Ile
 1               5                  10                  15

Val Leu Gly Ala Leu Leu Pro His Ser Val Trp Gly Pro Leu Pro Arg
                20                  25                  30

Phe Leu Gln Thr Trp Leu Arg Asn Tyr Leu Gly Gly Val Leu Leu Tyr
            35                  40                  45

Leu Leu Ser Gly Leu Leu Trp Cys Phe Tyr Ile Tyr Tyr Trp Lys Arg
         50                 55                  60

Asn Val His Val Pro Lys Asp Ala Ile Pro Ser Gln Arg Ala Met Leu
 65                 70                  75                  80

Leu Gln Ile Ser Val Ala Met Lys Ala Met Pro Trp Tyr Ser Leu Leu
                85                  90                  95

Pro Thr Val Ser Glu Tyr Leu Val Glu Thr Gly Trp Thr Lys Cys Tyr
            100                 105                 110

Pro Arg Leu Tyr Asn Val Gly Trp Leu Ala Tyr Leu Val Tyr Leu Ala
        115                 120                 125

Ile Tyr Leu Ile Ile Val Glu Phe Gly Ile Tyr Trp Met His Arg Glu
    130                 135                 140

Leu His Asp Ile Lys Pro Leu Tyr Lys Tyr Leu His Ala Thr His His
145                 150                 155                 160

Ile Tyr Asn Lys Gln Asn Thr Leu Ser Pro Phe Ala Gly Leu Ala Phe
                165                 170                 175

His Pro Leu Asp Gly Ile Leu Gln Ala Leu Pro His Ser Leu Cys Leu
            180                 185                 190

Phe Phe Met Pro Ile His Phe Thr Thr His Leu Ala Leu Ile Phe Ile
        195                 200                 205
```

```
Glu Gly Val Trp Thr Ala Asn Ile His Asp Cys Ile His Gly Lys Leu
    210                 215                 220
Trp Pro Val Met Gly Ala Gly Tyr His Thr Ile His His Thr Thr Tyr
225                 230                 235                 240
Arg His Asn Tyr Gly His Tyr Thr Ile Trp Met Asp Trp Met Phe Gly
                245                 250                 255
Thr Leu Arg Asp Pro Glu Glu Asp Gly Gly Lys Ala Met
            260                 265
```

```
<210> SEQ ID NO 29
<211> LENGTH: 1210
<212> TYPE: DNA
<213> ORGANISM: Triticum aestivum
<220> FEATURE:
<221> NAME/KEY: unsure
<222> LOCATION: (1130)
<223> OTHER INFORMATION: n = A, C, G, or T

<400> SEQUENCE: 29
```

| | | | | | |
|---|---|---|---|---|---|
| gcacgaggta | caacgagatc | ttcctcagcg | ccgtcgtgcc | gggcggcggc | ggctggtggc | 60 |
| gggcgctgcc | gcacccgctc | cgctcctggc | tgcgcaactg | catcggcggc | tacctcctct | 120 |
| acttcgccac | cggcttcctc | tggtgcttcg | tcatctacta | ctggaagcgc | aacgcctaca | 180 |
| tccccaaaga | tgctgtccct | acagtagaag | ctatgaagaa | gcaaataatt | gttgcatcaa | 240 |
| aggctatgcc | tttctactgt | gctcttccgt | ccgtatctga | gcacatgatt | gagagtggat | 300 |
| ggacacggtg | tttctttcat | atcagcgaag | ttggttggcc | tatgtacatt | atctatgtgt | 360 |
| ctctatatct | catctttgtg | gagttcggaa | tttactggat | gcacagagag | ttgcatgaca | 420 |
| taaagccact | atacaagcac | ctacatgcaa | cccaccacat | ttacaacaag | gagaataccc | 480 |
| tatcaccatt | tgctggacta | gcattccatc | cattggacgg | gatactgcaa | gccatatcgc | 540 |
| acgtgattgc | tctgttcctt | ctcccgatgc | acttcaggac | gcacattgct | ctcctattca | 600 |
| tagaggcggt | gtggacggca | acatccacg | actgcatcca | cggcaagatc | tggccggtga | 660 |
| tgggcgccgg | ctaccacacc | atccaccaca | cgacgtaccg | gcacaactat | ggccactaca | 720 |
| ccgtgtggat | ggactggctg | tttggcaccc | tccgcgagcc | ggaggatctc | ctcaagaagg | 780 |
| actgagctcg | tgcgtgcgag | cgcggtcttt | ccgtctctgt | agcaatgtga | agtgtagtag | 840 |
| aaagtgttga | ggcttaaccc | tcccatctgt | ttattctgct | gaaagatgtt | tgttgtgtgt | 900 |
| ttacgacagt | tagcggtgtg | ctgtttgagt | ctcagtctgg | taggtggaaa | taataaggtt | 960 |
| gtctatttag | ctttgttcct | ctgggatgcg | gtgaaatcaa | ggggcttgta | ccctttcgg | 1020 |
| cagcatgatg | gtttgtttg | ttgttatata | catagggctt | gatgctgttt | ctgctcccag | 1080 |
| ggtccatagt | ggtttggaga | aaatataaat | ccgggtggga | gtacgttggn | aaaaaaaaa | 1140 |
| aaaaaaaaaa | aaaaaaaaaa | aaaaaaaaaa | aaaaaaaaaa | aaaaaaaaaa | aaaaaaaaaa | 1200 |
| aaaaaaaaaa | | | | | | 1210 |

```
<210> SEQ ID NO 30
<211> LENGTH: 236
<212> TYPE: PRT
<213> ORGANISM: Triticum aestivum

<400> SEQUENCE: 30

Trp Trp Arg Ala Leu Pro His Pro Leu Arg Ser Trp Leu Arg Asn Cys
  1               5                  10                  15
Ile Gly Gly Tyr Leu Leu Tyr Phe Ala Thr Gly Phe Leu Trp Cys Phe
            20                  25                  30
```

```
Val Ile Tyr Tyr Trp Lys Arg Asn Ala Tyr Ile Pro Lys Asp Ala Val
         35                  40                  45

Pro Thr Val Glu Ala Met Lys Lys Gln Ile Ile Val Ala Ser Lys Ala
 50                  55                  60

Met Pro Phe Tyr Cys Ala Leu Pro Ser Val Ser Glu His Met Ile Glu
 65                  70                  75                  80

Ser Gly Trp Thr Arg Cys Phe Phe His Ile Ser Glu Val Gly Trp Pro
                 85                  90                  95

Met Tyr Ile Ile Tyr Val Ser Leu Tyr Leu Ile Phe Val Glu Phe Gly
                100                 105                 110

Ile Tyr Trp Met His Arg Glu Leu His Asp Ile Lys Pro Leu Tyr Lys
            115                 120                 125

His Leu His Ala Thr His His Ile Tyr Asn Lys Glu Asn Thr Leu Ser
    130                 135                 140

Pro Phe Ala Gly Leu Ala Phe His Pro Leu Asp Gly Ile Leu Gln Ala
145                 150                 155                 160

Ile Ser His Val Ile Ala Leu Phe Leu Leu Pro Met His Phe Arg Thr
                165                 170                 175

His Ile Ala Leu Leu Phe Ile Glu Ala Val Trp Thr Ala Asn Ile His
                180                 185                 190

Asp Cys Ile His Gly Lys Ile Trp Pro Val Met Gly Ala Gly Tyr His
            195                 200                 205

Thr Ile His His Thr Thr Tyr Arg His Asn Tyr Gly His Tyr Thr Val
    210                 215                 220

Trp Met Asp Trp Leu Phe Gly Thr Leu Arg Glu Pro
225                 230                 235

<210> SEQ ID NO 31
<211> LENGTH: 430
<212> TYPE: PRT
<213> ORGANISM: Arabidopsis thaliana

<400> SEQUENCE: 31

Met Ala Glu Thr Val His Ser Pro Ile Val Thr Tyr Ala Ser Met Leu
 1               5                  10                  15

Ser Leu Leu Ala Phe Cys Pro Pro Phe Val Ile Leu Leu Trp Tyr Thr
                20                  25                  30

Met Val His Gln Asp Gly Ser Val Thr Gln Thr Phe Gly Phe Phe Trp
            35                  40                  45

Glu Asn Gly Val Gln Gly Leu Ile Asn Ile Trp Pro Arg Pro Thr Leu
 50                  55                  60

Ile Ala Trp Lys Ile Ile Phe Cys Tyr Gly Ala Phe Glu Ala Ile Leu
 65                  70                  75                  80

Gln Leu Leu Leu Pro Gly Lys Arg Val Glu Gly Pro Ile Ser Pro Ala
                 85                  90                  95

Gly Asn Arg Pro Val Tyr Lys Ala Asn Gly Leu Ala Ala Tyr Phe Val
                100                 105                 110

Thr Leu Ala Thr His Leu Gly Leu Trp Trp Gly Ile Phe Asn Pro
            115                 120                 125

Ala Ile Val Tyr Asp His Leu Gly Glu Ile Phe Ser Ala Leu Ile Phe
    130                 135                 140

Gly Ser Phe Ile Phe Cys Val Leu Leu Tyr Ile Lys Gly His Val Ala
145                 150                 155                 160

Pro Ser Ser Ser Asp Ser Gly Ser Cys Gly Asn Leu Ile Ile Asp Phe
```

-continued

```
                165                 170                 175
Tyr Trp Gly Met Glu Leu Tyr Pro Arg Ile Gly Lys Ser Phe Asp Ile
            180                 185                 190
Lys Val Phe Thr Asn Cys Arg Phe Gly Met Met Ser Trp Ala Val Leu
        195                 200                 205
Ala Val Thr Tyr Cys Ile Lys Gln Tyr Glu Ile Asn Gly Lys Val Ser
    210                 215                 220
Asp Ser Met Leu Val Asn Thr Ile Leu Met Leu Val Tyr Val Thr Lys
225                 230                 235                 240
Phe Phe Trp Trp Glu Ala Gly Tyr Trp Asn Thr Met Asp Ile Ala His
                245                 250                 255
Asp Arg Ala Gly Phe Tyr Ile Cys Trp Gly Cys Leu Val Trp Val Pro
            260                 265                 270
Ser Val Tyr Thr Ser Pro Gly Met Tyr Leu Val Asn His Pro Val Glu
        275                 280                 285
Leu Gly Thr Gln Leu Ala Ile Tyr Ile Leu Val Ala Gly Ile Leu Cys
    290                 295                 300
Ile Tyr Ile Lys Tyr Asp Cys Asp Arg Gln Arg Gln Glu Phe Arg Arg
305                 310                 315                 320
Thr Asn Gly Lys Cys Leu Val Trp Gly Arg Ala Pro Ser Lys Ile Val
                325                 330                 335
Ala Ser Tyr Thr Thr Thr Ser Gly Glu Thr Lys Thr Ser Leu Leu Leu
            340                 345                 350
Thr Ser Gly Trp Trp Gly Leu Ala Arg His Phe His Tyr Val Pro Glu
        355                 360                 365
Ile Leu Ser Ala Phe Phe Trp Thr Val Pro Ala Leu Phe Asp Asn Phe
    370                 375                 380
Leu Ala Tyr Phe Tyr Val Leu Thr Leu Leu Phe Asp Arg Ala Lys
385                 390                 395                 400
Arg Asp Asp Asp Arg Cys Arg Ser Lys Tyr Gly Lys Tyr Trp Lys Leu
                405                 410                 415
Tyr Cys Glu Lys Val Lys Tyr Arg Ile Ile Pro Gly Ile Tyr
            420                 425                 430

<210> SEQ ID NO 32
<211> LENGTH: 271
<212> TYPE: PRT
<213> ORGANISM: Nicotiana tabacum

<400> SEQUENCE: 32

Met Asp Asp Tyr Leu Asn Leu Phe Ile Glu Glu Thr Ser Phe Tyr Asn
1               5                   10                  15
Arg Val Val Leu Gly Thr Phe Leu Pro Glu Ser Trp Trp Gly Pro Leu
                20                  25                  30
Pro His Trp Phe Gln Gly Trp Leu Arg Asn Tyr Ile Gly Gly Val Leu
            35                  40                  45
Leu Tyr Phe Ile Ser Gly Phe Leu Trp Cys Phe Tyr Ile Tyr Arg Leu
        50                  55                  60
Lys Arg Asn Val Tyr Ile Pro Lys Asp Ala Ile Pro Ser Asn Arg Ala
65                  70                  75                  80
Met Leu Leu Gln Ile Gly Val Ala Met Lys Ala Met Pro Phe Tyr Cys
                85                  90                  95
Ala Leu Pro Ser Leu Ser Glu Tyr Met Ile Val Asn Gly Trp Thr Lys
            100                 105                 110
```

```
Cys Phe Ser Arg Ile Ser Asp Val Gly Trp Leu Ser Tyr Leu Ile Tyr
            115                 120                 125

Met Ala Val Tyr Leu Val Ile Val Glu Phe Gly Ile Tyr Trp Met His
        130                 135                 140

Arg Glu Leu His Asp Ile Lys Leu Leu Tyr Lys Tyr Leu His Ala Thr
145                 150                 155                 160

His His Ile Tyr Asn Lys Gln Asn Thr Leu Ser Pro Phe Ala Gly Leu
                165                 170                 175

Ala Phe His Pro Leu Asp Gly Ile Leu Gln Ala Val Pro His Val Val
            180                 185                 190

Ala Leu Phe Leu Pro Glu His Phe Thr Thr His Ile Ala Leu Leu
        195                 200                 205

Phe Ile Glu Ala Ile Trp Thr Ala Asn Ile His Asp Cys Lys His Ala
    210                 215                 220

Lys Val Trp Pro Val Met Gly Ala Gly Tyr His Thr Ile His His Thr
225                 230                 235                 240

Thr Tyr Arg His Asn Tyr Gly His Tyr Thr Ile Trp Met Asp Trp Met
                245                 250                 255

Phe Gly Thr Leu Arg Asp Pro Val Glu Asp Glu Val Lys Lys Met
            260                 265                 270

<210> SEQ ID NO 33
<211> LENGTH: 271
<212> TYPE: PRT
<213> ORGANISM: Nicotiana tabacum

<400> SEQUENCE: 33

Met Glu Asp Tyr Leu Lys Gln Phe Val Glu Thr Ser Phe Tyr Asn
  1               5                  10                  15

Arg Leu Val Leu Gly Thr Phe Met Pro Glu Ser Trp Trp Gly Pro Leu
                20                  25                  30

Pro His Met Leu Gln Gly Trp Leu Arg Asn Tyr Ile Gly Gly Val Leu
            35                  40                  45

Leu Tyr Phe Ile Ser Gly Phe Leu Trp Cys Phe Tyr Ile Tyr His Leu
    50                  55                  60

Lys Arg Asn Val Tyr Ile Pro Lys Asp Ala Ile Pro Ser Asn Lys Ala
65                  70                  75                  80

Met Leu Leu Gln Ile Ser Val Ala Met Lys Ala Met Pro Trp Tyr Cys
                85                  90                  95

Ala Leu Pro Ser Leu Ser Glu Tyr Met Ile Glu Asn Gly Trp Thr Lys
            100                 105                 110

Cys Phe Ala Arg Ile Ser Asp Val Gly Trp Leu Ser Tyr Val Ile Tyr
            115                 120                 125

Ala Ala Ile Tyr Leu Val Ile Val Glu Phe Gly Ile Tyr Trp Met His
        130                 135                 140

Met Glu Leu His Asp Ile Lys Pro Leu Tyr Lys Tyr Leu His Ala Thr
145                 150                 155                 160

His His Ile Tyr Asn Lys Gln Asn Thr Leu Ser Pro Phe Ala Gly Leu
                165                 170                 175

Ala Phe His Pro Leu Asp Gly Ile Leu Gln Ala Val Pro His Val Val
            180                 185                 190

Ala Leu Leu Leu Val Pro Met His Phe Ser Thr His Ile Ala Leu Ile
        195                 200                 205

Phe Leu Glu Ala Leu Trp Thr Ala Asn Ile His Asp Cys Ile His Gly
    210                 215                 220
```

-continued

```
Lys Val Phe Pro Val Met Gly Ala Gly Tyr His Thr Ile His His Arg
225                 230                 235                 240

Thr Tyr Arg His Asn Tyr Gly His Tyr Thr Ile Trp Met Asp Trp Met
            245                 250                 255

Phe Gly Thr Leu Arg Asp Pro Val Glu Glu Asp Ala Lys Lys Met
            260                 265                 270
```

STEROL METABOLISM ENZYMES

This application is a divisional of U.S. application Ser. No. 09/443,041, filed Nov. 19, 1999, now U.S. Pat. No. 6,465,717, which claims the benefit of U.S. Provisional Application No. 60/109,283, filed Nov. 20, 1998.

FIELD OF THE INVENTION

This invention is in the field of plant molecular biology. More specifically, this invention pertains to nucleic acid fragments encoding sterol metabolism enzymes in plants and seeds.

BACKGROUND OF THE INVENTION

Conversion of 7-dehydrocholesterol to cholesterol is the last reaction in the cholesterol biosynthesis pathway catalyzed by the microsomal enzyme 7-dehydrocholesterol-delta 7 reductase (EC 1.3.1.21). Inhibiting the last step in cholesterol biosynthesis profoundly reduces tissue and plasma cholesterol concentrations and accumulates precursors that substantially slow hepatoma growth. Inhibiting late cholesterol synthesis also hinders the growth of rapidly enlarging malignant tumors (Xu, G. et al. (1996) *Hepatology* 24:440–445). Analyses of the cDNA encoding the human delta 7 sterol reductase shows that this enzyme is a membrane-bound protein containing 6 to 9 putative transmembrane segments and is structurally related to plant and yeast sterol reductases. The delta 7 sterol reductase is absent from yeast. Microsomes from *Saccharomyces cerevisiae* strains heterologously expressing the human delta 7 reductase cDNA remove the C7-8 double bond in 7-dehydrocholesterol in a NADPH-dependent manner (Moebius, F. F. et al. (1998) *Proc. Natl. Acad. Sci. USA* 95:1899–1902).

A microsomal preparation from seedlings of *Zea mays* catalyzed the NADPH-dependent reduction of the delta 7 bond of delta 5,7 cholestadienol giving the first in vitro evidence of the intermediacy of delta 5,7 sterols in plant sterol biosynthesis. In vitro inhibition of the plant delta 5,7 sterol delta 7 reductase by ammonium ion-containing fungicides was consistent with the previously proposed cationic mechanism involved in this reduction reaction (Taton, M. and Rahier, A. (1991) *Biochem. Biophys. Res. Commun.* 181:465–473). The NADPH-sterol delta-7 reductase from *Arabidopsis thaliana* has been cloned. The corresponding protein has significant sequence similarity with yeast delta 14 and delta 24 reductases and with human lamin B receptor. This protein is capable of efficiently reducing in vivo delta-5,7-ergosta- and cholesta-sterols, regardless of the structural variations on the side chain. The delta 7 reductase activity is preferentially associated with the endoplasmic reticulum membrane and uses NADPH as the reducing agent (Lecain, E. et al. (1996) *J. Biol. Chem.* 271:10866–10873).

Regulation of sterol biosynthesis in the terminal portion of the pathway represents an efficient mechanism by which the cell can control the production of sterol without disturbing the production of other essential mevalonate pathway products. Expression of ERG3, the gene encoding sterol C-5 desaturase, is increased in response to a mutation in the major isoform of HMG-CoA reductase which catalyzes the rate-limiting step of sterol biosynthesis. Mutations in non-auxotropic ergosterol biosynthetic genes downstream of squalene production result in an up-regulation of ERG3 expression. Absence of sterol esterification leads to a decrease in total intracellular sterol and ERG3 is a target of this negative regulation (Arthington-Skaggs, B. A. et al. (1996) *FEBS Lett.* 392:161–165). ERG3 is the structural gene in *Saccharomyces cerevisiae* for the sterol delta 5 desaturase that introduces the C5=6 unsaturation in ergosterol biosynthesis. Inactivated mutants of ERG3 fail to grow without added levels of delta 5 sterols in heme-deficient cells, and are unable to grow on the respiratory substrates glycerol and ethanol (Smith, S. J. and Parks, L. W. (1993) *Yeast* 9:1177–1187). A construct containing the promoter for the ERG3 gene fused to the bacterial lacZ reporter gene was placed in strains making aberrant sterols, and the effect of altered sterol composition on gene expression was monitored by beta-galactosidase activity. The absence of ergosterol resulted in a 35-fold increase in the expression of ERG3 as measured by beta-galactosidase activity. The level of ERG3 mRNA was increased as much as 9-fold in erg-mutant strains or wild-type strains inhibited in ergosterol biosynthesis by antifingal agents. The observed regulatory effects of ergosterol on ERG3 are specific for ergosterol, as several ergosterol derivatives failed to elicit the same controlling effect. These results demonstrate that ergosterol exerts a regulatory effect on gene transcription in *S. cerevisiae* (Smith, S. J. et al. (1996) *Mol. Cell Biol.* 16:5427–5432). A human cDNA clone homologous to fungal ERG3, a gene encoding sterol C-5 desaturase has been isolated. This gene is expressed in all normal human tissues examined (Matusushima, M. et al. (1996) *Cytogent. Cell Genet.* 74:252–254).

SUMMARY OF THE INVENTION

The present invention relates to isolated polynucleotides comprising a nucleotide sequence encoding a polypeptide of at least 30 amino acids that has at least 84% identity based on the Clustal method of alignment when compared to a polypeptide selected from the group consisting of a corn sterol delta-7 reductase polypeptide of SEQ ID NO:2, a rice sterol delta-7 reductase polypeptide of SEQ ID NO:4, a soybean sterol delta-7 reductase polypeptide of SEQ ID NO:6, a wheat sterol delta-7 reductase polypeptide of SEQ ID NO:8, or a corn sterol-C5 desaturase polypeptide of SEQ ID NO:2, a rice sterol-C5 desaturase polypeptide of SEQ ID NO:4, a soybean sterol-C5 desaturase polypeptide of SEQ ID NO:6, a wheat sterol-C5 desaturase polypeptide of SEQ ID NO:8. The present invention also relates to an isolated polynucleotide comprising the complement of the nucleotide sequences described above.

The present invention relates to isolated polynucleotides comprising a nucleotide sequence encoding a polypeptide of at least 30 amino acids that has at least 84% identity based on the Clustal method of alignment when compared to a polypeptide selected from the group consisting of SEQ ID NOs:10, 12, 14, 16, 18, 20, 22, 24, 26, 28 and 30. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, 13, 15, 17, 19, 21, 23, 25, 27, and 29 that codes for the polypeptide selected from the group consisting of SEQ ID NOs:2, 4, 6, 8, 10, 12, 14, 16, 18, 20, 22, 24, 26, 28, and 30. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a sterol delta-7 reductase or a sterol-C5 desaturase polypeptide of at least 30 amino acids comprising at least 84% homology based on the Clustal method of alignment compared to a polypeptide selected from the group consisting of SEQ ID NOs: 2, 4, 6, 8, 10, 12, 14, 16, 18, 20, 22, 24, 26, 28, and 30.

The present invention relates to a method of selecting an isolated polynucleotide that affects the level of expression of a sterol delta-7 reductase or a sterol-C5 desaturase polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a sterol delta-7 reductase or a sterol-C5 desaturase polypeptide in the host cell containing the isolated polynucleotide; and comparing the level of a sterol delta-7 reductase or a sterol-C5 desaturase polypeptide in the host cell containing the isolated polynucleotide with the level of a sterol delta-7 reductase or a sterol-C5 desaturase polypeptide in a plant cell that does not contain the isolated polynucleotide.

The present invention relates to a method of obtaining a nucleic acid fragment encoding a substantial portion of a sterol delta-7 reductase or a sterol-C5 desaturase polypeptide gene, preferably a plant sterol delta-7 reductase or a sterol-C5 desaturase polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences; and amplifying a nucleic acid fragment (preferably a cDNA inserted in a cloning vector) using the oligonucleotide primer. The amplified nucleic acid fragment preferably will encode a portion of a sterol delta-7 reductase or a sterol-C5 desaturase amino acid sequence.

The present invention also relates to a method of obtaining a nucleic acid fragment encoding all or a substantial portion of the amino acid sequence encoding a sterol delta-7 reductase or a sterol-C5 desaturase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a sterol delta-7 reductase or a sterol-C5 desaturase, the method comprising the steps of: (a) transforming a host cell with a chimeric gene comprising a nucleic acid fragment encoding a sterol delta-7 reductase or a sterol-C5 desaturase, operably linked to suitable regulatory sequences; (b) growing the transformed host cell under conditions that are suitable for expression of the chimeric gene wherein expression of the chimeric gene results in production of sterol delta-7 reductase or a sterol-C5 desaturase in the transformed host cell; (c) optionally purifying the sterol delta-7 reductase or a sterol-C5 desaturase expressed by the transformed host cell; (d) treating the sterol delta-7 reductase or a sterol-C5 desaturase with a compound to be tested; and (e) comparing the activity of the sterol delta-7 reductase or a sterol-C5 desaturase that has been treated with a test compound to the activity of an untreated sterol delta-7 reductase or a sterol-C5 desaturase, thereby selecting compounds with potential for inhibitory activity.

The present invention relates to a composition comprising the isolated polynucleotide of the present invention.

The present invention relates to a composition comprising a polypeptide of the present invention.

The present invention relates to an expression cassette comprising an isolated polynucleotide of the present invention operably linked to a promoter.

The present invention relates to a method for positive selection of a transformed cell comprising:

(a) transforming a plant cell, preferably a monocot or a dicot, with a chimeric gene of the present invention or an expression cassette of the present invention; and (b) growing the transformed plant under conditions allowing expression of the polynucleotide in an amount sufficient to modify the amount of sterol in the cell to provide a positive selection means.

The present invention relates to the method of the present invention, wherein the plant cell is a monocot.

The present invention relates to the method of the present invention, wherein the plant cell is a dicot.

As used herein, the following terms shall apply:

"Sterol metabolism enzymes" refers to sterol delta-7 reductase and/or steorl-C5 desaturase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 (FIGS. 1A–1B) shows a comparison of the amino acid sequences of the corn, rice, soybean, and wheat (SEQ ID NOs:2, 18, 20, and 22, respectively) sterol delta-7 reductases compared to the Arabidopsis thaliana enzyme (SEQ ID NO:31, Genbank Accession No. 1245182).

FIG. 2 (FIGS. 2A–2B) shows a comparison of the amino acid sequences of the corn, rice, soybean, and wheat (SEQ ID NOs:24, 26, 28, and 30, respectively) sterol-C-5 desaturases compared to the Nicotiana tabacum enzymes (SEQ ID NOs:32 and 33, Genbank Accession Nos. 2226627 and 4140398, respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide

TABLE 1

Sterol Metabolism Enzymes

| Protein | Plant [Species] | Clone Designation | SEQ ID NO: (Nuc) | SEQ ID NO: (AA) |
| --- | --- | --- | --- | --- |
| Sterol delta-7 reductase | maize [Zea mays] | contig of: cep7.pk0018.a6, cep7.pk0019.a3 | 1 | 2 |
| Sterol delta-7 reductase | rice [Oryza sativa] | rl0n.pk083 a21 | 3 | 4 |
| Sterol delta-7 reductase | soybean [Glycine max] | sfl1.pk0030.b7 | 5 | 6 |
| Sterol delta-7 reductase | wheat-common [Triticum aestivum] | wl1n.pk0001.g5 | 7 | 8 |
| Sterol-C5-desaturase | maize [Zea mays] | ceb5.pk0078.d4 | 9 | 10 |
| Sterol-C5-desaturase | rice [Oryza sativa] | rlr2.pk0028.c11 | 11 | 12 |
| Sterol-C5-desaturase | soybean [Glycine max] | sfl1.pk0107.g5 | 13 | 14 |
| Sterol-C5-desaturase | wheat-common [Triticum aestivum] | wr1.pk0107.a5 | 15 | 16 |
| Sterol delta-7 reductase | rice [Oryza sativa] | rl0n.pk083.a21:fis | 17 | 18 |
| Sterol delta-7 reductase | soybean [Glycine max] | sfl1.pk0030.b7:fis | 19 | 20 |
| Sterol delta-7 reductase | wheat-common [Triticum aestivum] | wl1n.pk0001.g5:fis | 21 | 22 |
| Sterol-C5-desaturase | maize [Zea mays] | cta1n.pk0078.cl:fis | 23 | 24 |
| Sterol-C5-desaturase | rice [Oryza sativa] | rlr2.pk0028c11:fis | 25 | 26 |
| Sterol-C5-desaturase | soybean [Glycine max] | sfl1.pk1017.g5:fis | 27 | 28 |
| Sterol-C5-desaturase | wheat-common [Triticum aestivum] | wr1.pk0107.a5:fis | 29 | 30 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, 15, 17, 19, 21, 23, 25, 27, 29, and the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences may be used in methods of selecting an isolated polynucleotide that affects the expression of a polypeptide in a host cell. A method of selecting an isolated polynucleotide that affects the level of expression of a polypeptide (such as a sterol metabolism enzyme) in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410). In general, a sequence often or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sterol metabolism enzyme have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other sterol delta-7 reductase or a sterol-C5 desaturase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as sterol delta-7 reductase or a sterol-C5 desaturase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1–34; Maniatis).

The nucleic acid fragments of the instant invention may be used to create transgenic plants in which the disclosed sterol delta-7 reductase or sterol-C5 desaturase are present at higher or lower levels than normal or in cell types or developmental stages in which they are not normally found. This would have the effect of altering the ratio of saturated to unsaturated sterols in those cells without disturbing the production of other essential mevalonate pathway products.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) EMBO J. 4:2411–2418; De Almeida et al. (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), or nuclear localization signals (Raikhel (1992) Plant Phys. 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sterol metabolism enzyme. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in sterol metabolism, which in turn affects the accumulation of structural membrane sterols and their related hormones, such as brassinosteroids, that are produced from plant sterols (Altmann (1998) *Curr Op Plant Bio* 1:378–383; Rouleau et al. (1999) *J Biol Chem* 274:20925–20930). Accordingly, inhibition of the activity of one or more of the enzymes described herein could lead to inhibition or alteration of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cbn2 | Corn Developing Kernel Two Days After Pollination | cbn2.pk0007.h11<br>cbn2.pk0054.f4 |
| ceb5 | Corn Embryo 30 Days After Pollination | ceb5.pk0013.g1<br>ceb5.pk0078.d4 |
| cen3n | Corn Endosperm 20 Days After Pollination* | cen3n.pk0157.h1 |
| cep7 | Corn 7 Day Old Epicotyl; Grown in Light | cep7.pk0018.a6<br>cep7.pk0019.a3 |
| cr1n | Corn Root From 7 Day Old Seedlings* | cr1n.pk0141.e2 |
| cta1n | Corn Tassel* | cta1n.pk0078.c1 |
| rl0n | Rice 15 Day Old Leaf* | rl0n.pk083.a21 |
| rlr2 | Rice Leaf 15 Days After Germination, 2 Hours After Infection of Strain *Magaporthe grisea* 4360-R-62 (AVR2-YAMO); Resistant | rlr2.pk0028.c11 |
| sfl1 | Soybean Immature Flower | sfl1.pk0030.b7<br>sfl1.pk0107.g5 |
| src3c | Soybean 8 Day Old Root Infected With Cyst Nematode | src3c.pk002.g3 |
| wl1n | Wheat Leaf From 7 Day Old Seedling* | wl1n.pk0001.g5 |
| wr1 | Wheat Root From 7 Day Old Seedling | wr1.pk0107.a5 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding sterol metabolism enzyme were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Sterol Delta-7 Reductase

The BLASTX search using the EST sequences from clones listed in Table 3 revealed similarity of the polypeptides encoded by the cDNAs to sterol delta-7 reductase from *Arabidopsis thaliana* (NCBI Accession No. gi 1245182). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to Sterol Delta-7 Reductase

| Clone | Status | BLAST pLog Score<br>1245182 |
|---|---|---|
| cep7.pk0019.a3<br>cep7.pk0018.a6 | Contig | 20.52 |
| rl0n.pk083.a21 | EST | 34.05 |
| src3c.pk002.g3<br>sfl1.pk0030.b7 | Contig | 67.00 |
| wl1n.pk0001.g5 | EST | 57.40 |
| sfl1.pk0030.b7:fis | FIS | 254.00 |
| rl0n.pk083.a21:fis | FIS | 254.00 |
| wl1n.pk0001.g5:fis | FIS | 254.00 |

FIG. 1 presents an alignment of the amino acid sequences set forth in SEQ ID NOs:2, 18, 20, and 22, and the *Arabidopsis thaliana* sequence (SEQ ID NO:31). The data in Table 4 represents a calculation of the percent identity of the amino acid sequences set forth in SEQ ID NOs:2, 18, 20, and 22, and the *Arabidopsis thaliana* sequence (SEQ ID NO:31).

TABLE 4

Percent Identity of Amino Acid Sequences Deduced From the Nucleotide Sequences of cDNA Clones Encoding Polypeptides Homologous to Sterol Delta-7 Reductase

| SEQ ID NO. | Percent Identity to<br>1245182 |
|---|---|
| 2 | 63.5% |
| 18 | 81.6% |
| 20 | 82.8% |
| 22 | 81.4% |

Sequence alignments and percent identity calculations were performed using the Megalign program of the LASER- GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a sterol delta-7 reductase. These sequences represent the first monocot and soybean sequences encoding sterol delta-7 reductase.

Example 4

Characterization of cDNA Clones Encoding Sterol-C5 Desaturase

The BLASTX search using the EST sequences from clones listed in Table 5 revealed similarity of the polypeptides encoded by the cDNAs to sterol-C5 desaturases from *Nicotiana tabacum* (NCBI Accession No. gi 4426627 for the corn sequence, and NCBI Accession No. gi 4140398). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to Sterol-C5 Desaturase

| Clone | Status | BLAST pLog Score 4426627/4140398 |
|---|---|---|
| ceb5.pk0078.d4 | Contig | 135.00 |
| cbn2.pk0054.f4 | | |
| cta1n.pk0078.c1 | | |
| ceb5.pk0013.g1 | | |
| cen3n.pk0157.h1 | | |
| cr1n.pk0141.e2 | | |
| cbn2.pk0007.h11 | | |
| rlr2.pk0028.c11 | FIS | 13.70 |
| sfl1.pk0107.g5 | Contig | 38.70 |
| wr1.pk0107.a5 | EST | 38.70 |
| cta1n.pk0078.c1:fis | FIS | 96.40 |
| rlr2.pk0028.c11:fis | FIS | 125.00 |
| sfl1.pk0107.g5:fis | FIS | 133.00 |
| wr1.pk0107.a5:fis | FIS | 118.00 |

FIG. 2 presents an alignment of the amino acid sequences set forth in SEQ ID NOs:24, 26, 28, and 30, and the *Nicotiana tabacum* sequences (SEQ ID NO:32 most closely related to SEQ ID NO:24, and SEQ ID NO:33 that has best BLAST homology with SEQ ID NOs:26, 28, and 30). The data in Table 6 represents a calculation of the percent identity of the amino acid sequences set forth in SEQ ID NOs:24, 26, 28, and 30, and the *Nicotiana tabacum* sequences (SEQ ID NO:32 most closely related to SEQ ID NO:24, and SEQ ID NO:33 that matches best with SEQ ID NOs:26, 28, and 30).

TABLE 6

Percent Identity of Amino Acid Sequences Deduced From the Nucleotide Sequences of cDNA Clones Encoding Polypeptides Homologous to Sterol-C5 Desaturase

| SEQ ID NO. | Percent Identity to 4426627 |
|---|---|
| 24 | 80.1% |

| SEQ ID NO. | Percent Identity to 4140398 |
|---|---|
| 26 | 73.2% |
| 28 | 75.5% |
| 30 | 76.7% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of corn, rice, soybean, and wheat sterol-C5 desaturase. These sequences represent the first monocot and soybean sequences encoding sterol-C5 desaturase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont BioliStic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Sterol Metabolism Enzyme The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for sterol delta-7 reductase are presented by Lecain et al. (1996) *J Biol Chem* 271:10866–10873. Assays for sterol-C-5 desaturase are presented by Taton and Rahier (1996) *Arch Biochem Biophys* 325:279–288.

What is claimed is:

1. An isolated polynucleotide comprising:
   (a) a nucleotide sequence encoding a polypeptide having sterol C5-desaturase activity, wherein the polypeptide has an amino acid sequence of at least 90% sequence identity, based on the Clustal alignment method, when compared to SEQ ID NO:28, or
   (b) a complement of the nucleotide sequence, wherein the complement and the nucleotide sequence have the same number of nucleotides and are 100% complementary.

2. The polynucleotide of claim 1, wherein the amino acid sequence of the polypeptide has at least 95% sequence identity, based on the Clustal alignment method, when compared to SEQ ID NO:28.

3. The polynucleotide of claim 1, wherein the amino acid sequence of the polypeptide comprises SEQ ID NO:28.

4. The polynucleotide of claim 1 wherein the nucleotide sequence comprises SEQ ID NO:27.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *